(12) United States Patent
Smith

(10) Patent No.: US 11,153,970 B1
(45) Date of Patent: Oct. 19, 2021

(54) APPARATUS WITH ELECTRICAL COMPONENTS END MOUNTED TO PRINTED CIRCUIT BOARD

(71) Applicant: ATL Technology, LLC, Springville, UT (US)

(72) Inventor: David Smith, Draper, UT (US)

(73) Assignee: ATL TECHNOLOGY, LLC, Springville, UT (US)

(*) Notice: Subject to any disclaimer, the term of this patent is extended or adjusted under 35 U.S.C. 154(b) by 0 days.

(21) Appl. No.: 17/022,056

(22) Filed: Sep. 15, 2020

Related U.S. Application Data

(60) Provisional application No. 63/054,142, filed on Jul. 20, 2020.

(51) Int. Cl.
*H05K 1/11* (2006.01)

(52) U.S. Cl.
CPC .... *H05K 1/111* (2013.01); *H05K 2201/10015* (2013.01); *H05K 2201/10106* (2013.01); *H05K 2201/10734* (2013.01); *H05K 2201/10992* (2013.01)

(58) Field of Classification Search
CPC .............................................. H05K 1/11–119
See application file for complete search history.

(56) References Cited

U.S. PATENT DOCUMENTS

| | | | |
|---|---|---|---|
| 4,769,906 A | 9/1988 | Purpura et al. | |
| 5,281,762 A | 1/1994 | Long et al. | |
| 8,292,655 B1 | 10/2012 | Ling et al. | |
| 10,403,418 B2 | 9/2019 | Aoyagi et al. | |
| 10,510,918 B2 | 12/2019 | Hu et al. | |
| 2016/0072989 A1 | 3/2016 | Kennedy, II | |
| 2018/0219310 A1 | 8/2018 | Lukofsky et al. | |

FOREIGN PATENT DOCUMENTS

| | | |
|---|---|---|
| AU | 2015315524 B2 | 9/2018 |
| CN | 106797428 A | 5/2017 |
| EP | 3190946 B1 | 5/2019 |
| EP | 3536220 A1 | 9/2019 |
| JP | 2008181817 | 8/2008 |
| JP | 2009170142 | 7/2009 |
| JP | 5871217 | 3/2016 |
| JP | 5962275 B2 | 8/2016 |
| JP | 2017532100 | 11/2017 |
| KR | 101318543 | 10/2013 |
| WO | 2009139041 A1 | 11/2009 |
| WO | 2016040156 | 3/2016 |

*Primary Examiner* — Jeremy C Norris
(74) *Attorney, Agent, or Firm* — Kunzler Bean & Adamson

(57) ABSTRACT

Disclosed herein is an apparatus that comprises a printed circuit board having a first major surface, a second major surface opposite the first major surface, and a minor surface perpendicular to the first major surface and the second major surface. The apparatus also comprises an electronic component that comprises a ball grid array, having spaced apart solder balls, on a mounting surface of the electronic component. The electronic component is mounted to the minor surface of the printed circuit board such that the mounting surface is parallel to the minor surface and perpendicular to the first major surface and the second major surface. The solder balls of the ball grid array are electrically connected to both the first major surface and the second major surface of the printed circuit board.

21 Claims, 14 Drawing Sheets

APPARATUS WITH ELECTRICAL COMPONENTS END MOUNTED TO PRINTED CIRCUIT BOARD

CROSS-REFERENCED TO RELATED APPLICATION

This application claims the benefit of U.S. Provisional Patent Application No. 63/054,142, filed Jul. 20, 2020, which is incorporated herein by reference.

FIELD

The present disclosure relates generally to electronic devices, and more particularly to mounting electrical components to printed circuit boards of electronic devices.

BACKGROUND

Many electronic devices include electrical components mounted to a printed circuit board. The printed circuit board commonly employs mounting pads, which are configured to conduct electrical signals. Electrical components having a ball-grid array ("BGA") of solder balls can be mounted to the mounting pads using Surface Mount Technology ("SMT") techniques. Typical SMT techniques involve mounting electrical components onto a major surface (e.g., broad surface) of the printed circuit board.

While conventional SMT techniques are appropriate for some electronic devices, for other electrical devices, such as those that demand a streamlined profile, conventional SMT techniques are inadequate. A method of utilizing SMT principles to mount electrical components to a printed circuit board that promotes a low profile of the corresponding electronic device is desirable.

SUMMARY

The subject matter of the present application has been developed in response to the present state of the art, and in particular, in response to the problems and needs of conventional devices or products with surface mount technology that have not yet been fully solved. The subject matter of the present application has been developed to provide an end mount electrical connection to a printed circuit board that overcomes many of the shortcomings of the prior art.

Disclosed herein is an apparatus that comprises a printed circuit board having a first major surface, a second major surface opposite the first major surface, and a minor surface perpendicular to the first major surface and the second major surface. The apparatus also comprises an electronic component that comprises a ball grid array, having spaced apart solder balls, on a mounting surface of the electronic component. The electronic component is mounted to the minor surface of the printed circuit board such that the mounting surface is parallel to the minor surface and perpendicular to the first major surface and the second major surface. The solder balls of the ball grid array are electrically connected to both the first major surface and the second major surface of the printed circuit board. The apparatus further comprises gussets. A first one of the gussets is between and in contact with the electronic component and the first major surface and a second one of the gussets is between and in contact with the electronic component and the second major surface. The preceding subject matter of this paragraph characterizes example 1 of the present disclosure.

The printed circuit board is flexible. The preceding subject matter of this paragraph characterizes example 2 of the present disclosure, wherein example 2 also includes the subject matter according to example 1, above.

The gussets are made of an epoxy material. The preceding subject matter of this paragraph characterizes example 3 of the present disclosure, wherein example 3 also includes the subject matter according to any one of examples 1 or 2, above.

The first one of the gussets is between and in contact with the mounting surface of the electronic component and the first major surface of the printed circuit board. The second one of the gussets is between and in contact with the mounting surface of the electronic component and the second major surface of the printed circuit board. The preceding subject matter of this paragraph characterizes example 4 of the present disclosure, wherein example 4 also includes the subject matter according to any one of examples 1-3, above.

The first one and the second one of the gussets are interposed between and do not overlay the solder balls of the ball grid array. The preceding subject matter of this paragraph characterizes example 5 of the present disclosure, wherein example 5 also includes the subject matter according to example 4, above.

Each one of the first one and the second one of the gussets is interposed between and overlays respective ones of the solder balls of the ball grid array. The preceding subject matter of this paragraph characterizes example 6 of the present disclosure, wherein example 6 also includes the subject matter according to example 4, above.

The electronic component comprises opposing side surfaces that are angled relative to the mounting surface. The first one of the gussets is between and in contact with a first one of the opposing side surfaces of the electronic component and the first major surface. The second one of the gussets is between and in contact with a second one of the opposing side surfaces of the electronic component and the first major surface. The preceding subject matter of this paragraph characterizes example 7 of the present disclosure, wherein example 7 also includes the subject matter according to any one of examples 1-6, above.

A third one of the gussets is between and in contact with the first one of the opposing side surfaces of the electronic component and the second major surface. A fourth one of the gussets is between and in contact with the second one of the opposing side surfaces of the electronic component and the second major surface. The preceding subject matter of this paragraph characterizes example 8 of the present disclosure, wherein example 8 also includes the subject matter according to example 7, above.

A fifth one of the gussets is between and in contact with the mounting surface of the electronic component and the first major surface of the printed circuit board. A sixth one of the gussets is between and in contact with the mounting surface of the electronic component and the second major surface of the printed circuit board. The preceding subject matter of this paragraph characterizes example 9 of the present disclosure, wherein example 9 also includes the subject matter according to example 8, above.

Also disclosed herein is an apparatus that comprises a printed circuit board having a first major surface, a second major surface opposite the first major surface, and a minor surface perpendicular to the first major surface and the second major surface. The apparatus also comprises an electronic component comprising a ball grid array, having spaced apart solder balls, on a mounting surface of the electronic component. The electronic component is mounted to the minor surface of the printed circuit board such that the mounting surface is parallel to the minor surface and perpendicular to the first major surface and the second major surface. The solder balls of the ball grid array are electrically connected to both the first major surface and the second major surface of the printed circuit board. The apparatus further comprises a support bracket in contact with the mounting surface of the electronic component, the first major surface of the printed circuit board, and the second major surface of the printed circuit board. The preceding subject matter of this paragraph characterizes example 10 of the present disclosure.

The support bracket is perpendicular to the printed circuit board. The preceding subject matter of this paragraph characterizes example 11 of the present disclosure, wherein example 11 also includes the subject matter according to example 10, above.

The support bracket is interposed between the solder balls of the ball grid array. The preceding subject matter of this paragraph characterizes example 12 of the present disclosure, wherein example 12 also includes the subject matter according to any one of examples 10 or 11, above.

The printed circuit board comprises a first slot formed in and extending from the minor surface of the printed circuit board. The support bracket comprises a second slot. The support bracket is received in the first slot of the printed circuit board. The printed circuit board is received in the second slot of the support bracket. The preceding subject matter of this paragraph characterizes example 13 of the present disclosure, wherein example 13 also includes the subject matter according to any one of examples 10-12, above.

The support bracket comprises an intermediate portion and a supplemental engagement portion. The intermediate portion is in contact with the mounting surface of the electronic component. The supplemental engagement portion wraps around at least a portion of the electronic component. The preceding subject matter of this paragraph characterizes example 14 of the present disclosure, wherein example 14 also includes the subject matter according to any one of examples 10-13, above.

The intermediate portion is perpendicular to the supplemental engagement portion. The preceding subject matter of this paragraph characterizes example 15 of the present disclosure, wherein example 15 also includes the subject matter according to example 14, above.

The apparatus further comprises gussets. A first one of the gussets is between and in contact with the electronic component and the first major surface and a second one of the gussets is between and in contact with the electronic component and the second major surface. The preceding subject matter of this paragraph characterizes example 16 of the present disclosure, wherein example 16 also includes the subject matter according to any one of examples 10-15, above.

Additionally disclosed herein is an apparatus that comprises a printed circuit board having a first major surface, a second major surface opposite the first major surface, and a minor surface perpendicular to the first major surface and the second major surface. The apparatus also comprises an electronic component comprising a ball grid array, having spaced apart solder balls, on a mounting surface of the electronic component. The electronic component is mounted to the minor surface of the printed circuit board such that the mounting surface is parallel to the minor surface and perpendicular to the first major surface and the second major surface. The solder balls of the ball grid array are electrically connected to both the first major surface and the second major surface of the printed circuit board. The apparatus additionally comprises a second electronic component and a third electronic component mounted to a second minor surface and a third minor surface of the printed circuit board, respectively. The second minor surface and the third minor surface are parallel to the minor surface of the printed circuit board. The preceding subject matter of this paragraph characterizes example 17 of the present disclosure.

The electronic component is interposed between the second electronic component and the third electronic component. The second minor surface and the third minor surface of the printed circuit board are spaced apart from the minor surface of the printed circuit board. The second minor surface and the third minor surface of the printed circuit board are defined by an end of a corresponding one of two prongs of the printed circuit board. The two prongs extend away from the minor surface of the printed circuit board in a direction perpendicular to the minor surface. The preceding subject matter of this paragraph characterizes example 18 of the present disclosure, wherein example 18 also includes the subject matter according to example 17, above.

The electronic component is a camera, the second electronic component is a first light-emitting diode (LED), and the third electronic component is a second LED. The preceding subject matter of this paragraph characterizes example 19 of the present disclosure, wherein example 19 also includes the subject matter according to any one of examples 17 or 18, above.

The apparatus further comprises a capacitor mounted onto the first major surface of the printed circuit board, in close proximity to the electronic component, and electrically coupled with the electronic component to mitigate interference and signal or image degradation associated with the electronic component. The preceding subject matter of this paragraph characterizes example 20 of the present disclosure, wherein example 20 also includes the subject matter according to any one of examples 17-19, above.

Also disclosed herein is a method of automatically making an apparatus. The method comprises individually picking light-emitting diodes (LEDs) from a carrier tape, comprising a plurality of LEDs, with an automated tool. The method further comprises individually flipping over each one of the LEDs picked from the carrier tape with and relative to the automated tool and, after flipping over each one of the LEDs, placing the LEDs relative to each other to form an LED nest comprising a plurality of LEDs arranged in a predetermined pattern corresponding with a pattern of electrical contact pads on a printed circuit board. The method additionally comprises optically verifying an orientation and a location of electrical contact pads of a printed circuit board using a sensor and, based on a verified orientation and a verified location of the electrical contact pads, moving the printed circuit board, with the automated tool or a second automated tool, such that corresponding ones of the electrical contact pads of the printed circuit board are aligned with the LEDs in the LED nest. The method further comprises applying solder paste to the corresponding ones of the electrical contact pads and the LEDs and reflowing the solder paste applied to the electrical contact pads and the LEDs. The method additionally comprises optically verifying a location of solder balls of a camera, using the sensor or a second sensor and, based on the verified orientation and the verified location of the electrical contact pads and a verified location of the solder balls of the camera, moving the camera such that the solder balls of the camera are aligned with corresponding ones of the electrical contact pads. The method further comprises applying solder paste to the solder balls and the electrical contact pads aligned with the solder balls and reflowing the solder paste applied to the solder balls and the electrical contact pads aligned with the solder balls. The preceding subject matter of this paragraph characterizes example 21 of the present disclosure.

The described features, structures, advantages, and/or characteristics of the subject matter of the present disclosure may be combined in any suitable manner in one or more embodiments and/or implementations. In the following description, numerous specific details are provided to impart a thorough understanding of embodiments of the subject matter of the present disclosure. One skilled in the relevant art will recognize that the subject matter of the present disclosure may be practiced without one or more of the specific features, details, components, materials, and/or methods of a particular embodiment or implementation. In other instances, additional features and advantages may be recognized in certain embodiments and/or implementations that may not be present in all embodiments or implementations. Further, in some instances, well-known structures, materials, or operations are not shown or described in detail to avoid obscuring aspects of the subject matter of the present disclosure. The features and advantages of the subject matter of the present disclosure will become more fully apparent from the following description and appended claims, or may be learned by the practice of the subject matter as set forth hereinafter.

BRIEF DESCRIPTION OF THE DRAWINGS

In order that the advantages of the subject matter may be more readily understood, a more particular description of the subject matter briefly described above will be rendered by reference to specific embodiments that are illustrated in the appended drawings. Understanding that these drawings depict only typical embodiments of the subject matter and are not therefore to be considered to be limiting of its scope, the subject matter will be described and explained with additional specificity and detail through the use of the drawings, in which.

DETAILED DESCRIPTION

Reference throughout this specification to "one embodiment," "an embodiment," or similar language means that a particular feature, structure, or characteristic described in connection with the embodiment is included in at least one embodiment of the present disclosure. Appearances of the phrases "in one embodiment," "in an embodiment," and similar language throughout this specification may, but do not necessarily, all refer to the same embodiment. Similarly, the use of the term "implementation" means an implementation having a particular feature, structure, or characteristic described in connection with one or more embodiments of the present disclosure, however, absent an express correlation to indicate otherwise, an implementation may be associated with one or more embodiments.

Figure 1:
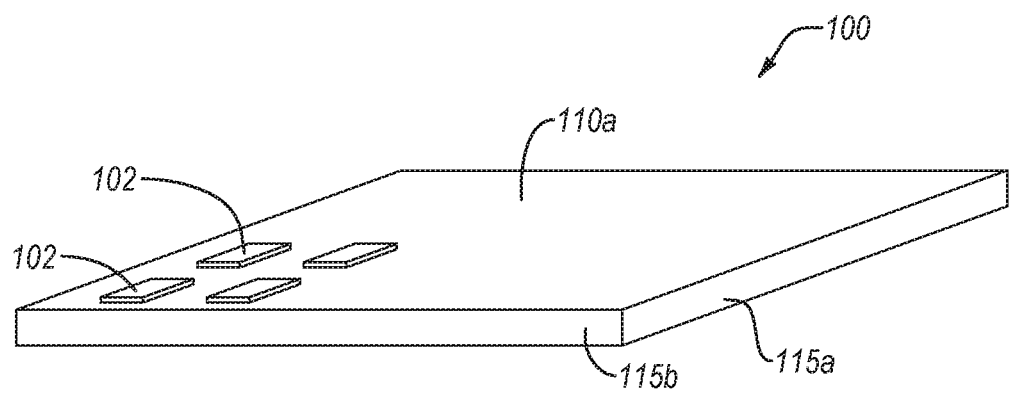
FIG. 1 illustrates a perspective view of a typical printed circuit board with an array of connectors, according to one or more examples of the present disclosure.
Figure 2:
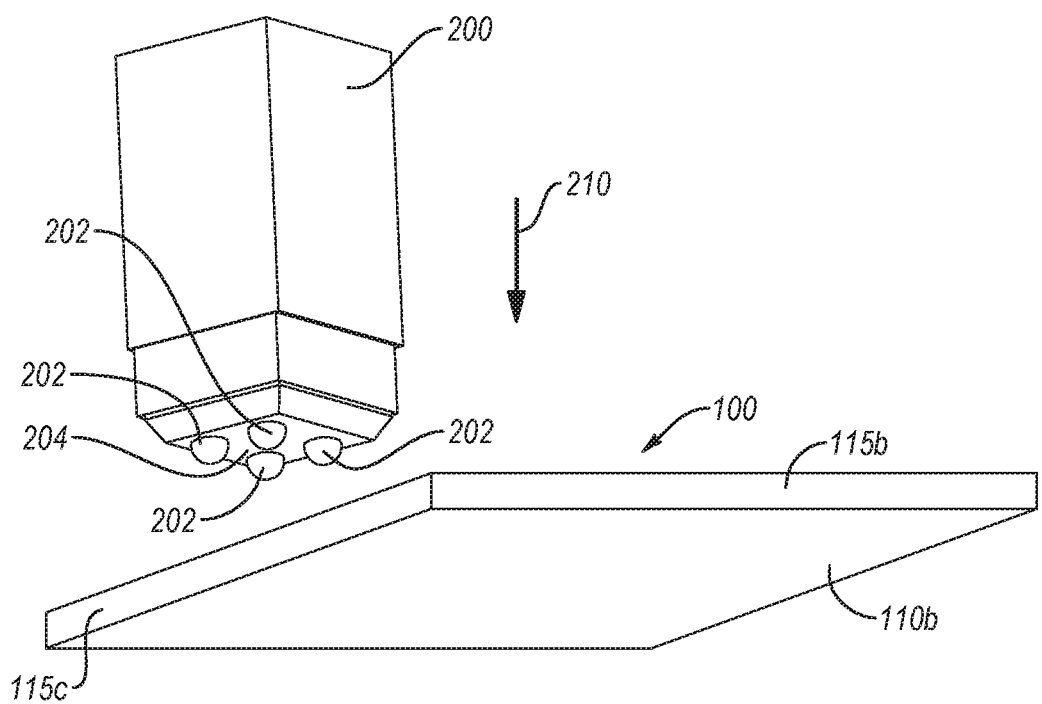
FIG. 2 illustrates a perspective view of an electronic component with a ball grid array and a printed circuit board showing the typical manner in which electronic component is connected to the printed circuit board, according to one or more examples of the present disclosure.

Referring to FIG. 1, one embodiment of a circuit board 100 is shown. The circuit board 100 includes mounting pads 102 which are configured to conduct electrical signals. Referring to FIG. 2, a normal mounting procedure for a ball-grid array ("BGA") employing Surface Mount Technology ("SMT") is shown. As the name implies, all SMT components are intended to be mounted "surface-to-surface" to a circuit board, as opposed to through-hole technology, which utilized pin-grid arrays ("PGA"). In addition to electronic components with BGA mounting, SMT is utilized for connecting LED's, resistors, capacitors, ICs and nearly all small electronic components in use today.

FIG. 2 further shows a perspective view of an electronic component 200 with a ball grid array of solder balls 202 which is being positioned such that the solder balls 202 of the ball grid array of the electronic component 200 interfaces with the mounting pads 102 of the circuit board 100. The solder balls 202 are positioned on a connecting surface 204 of the electronic component 200. As shown by arrow 210, the electronic component 200 is moved down to connect the electronic component 200 to the circuit board 100.

In conventional SMT mounting techniques, a major surface (e.g., broad surface) of the electronic component is mated with a major surface (e.g., broad surface) of the circuit board 100. As shown in FIGS. 1 and 2, the circuit board 100 includes two major surfaces, a top major surface 110a (e.g., first major surface as shown in FIG. 1) and a bottom major surface 110b (e.g., second major surface as shown in FIG. 2). The circuit board 100 also includes four minor surfaces or edges, with three of the minor surfaces 115a, 115b, 115c being shown. Each of the minor surfaces, or edges, may generally be referred to as a minor surface 115. The minor surfaces 115 are typically small in comparison to the major surfaces of the circuit board 100. The minor surfaces 115 have a width equal to or no more than the thickness of the circuit board 100. Moreover, the minor surfaces 115 of the circuit board 100 are perpendicular to the top major surface 110a and the bottom major surface 110b. Although the circuit board 100 only has four minor surfaces 115, a circuit board 100 may have more or less minor surfaces 115 depending on the shape of the circuit board 100. As shown, according to conventional methods, the connecting surface 204 of the electronic component 200, when connected, is parallel and adjacent to the top major surface 110a or bottom major surface 110b of the circuit board 100. For some electrical components having multiple (e.g., four) possible mounting surfaces and mounting orientations, regardless of which one of the mounting surfaces is mounted to the major surface of the circuit board 100, that mounting surface is parallel to the major surface of the circuit board 100.

Figure 3:
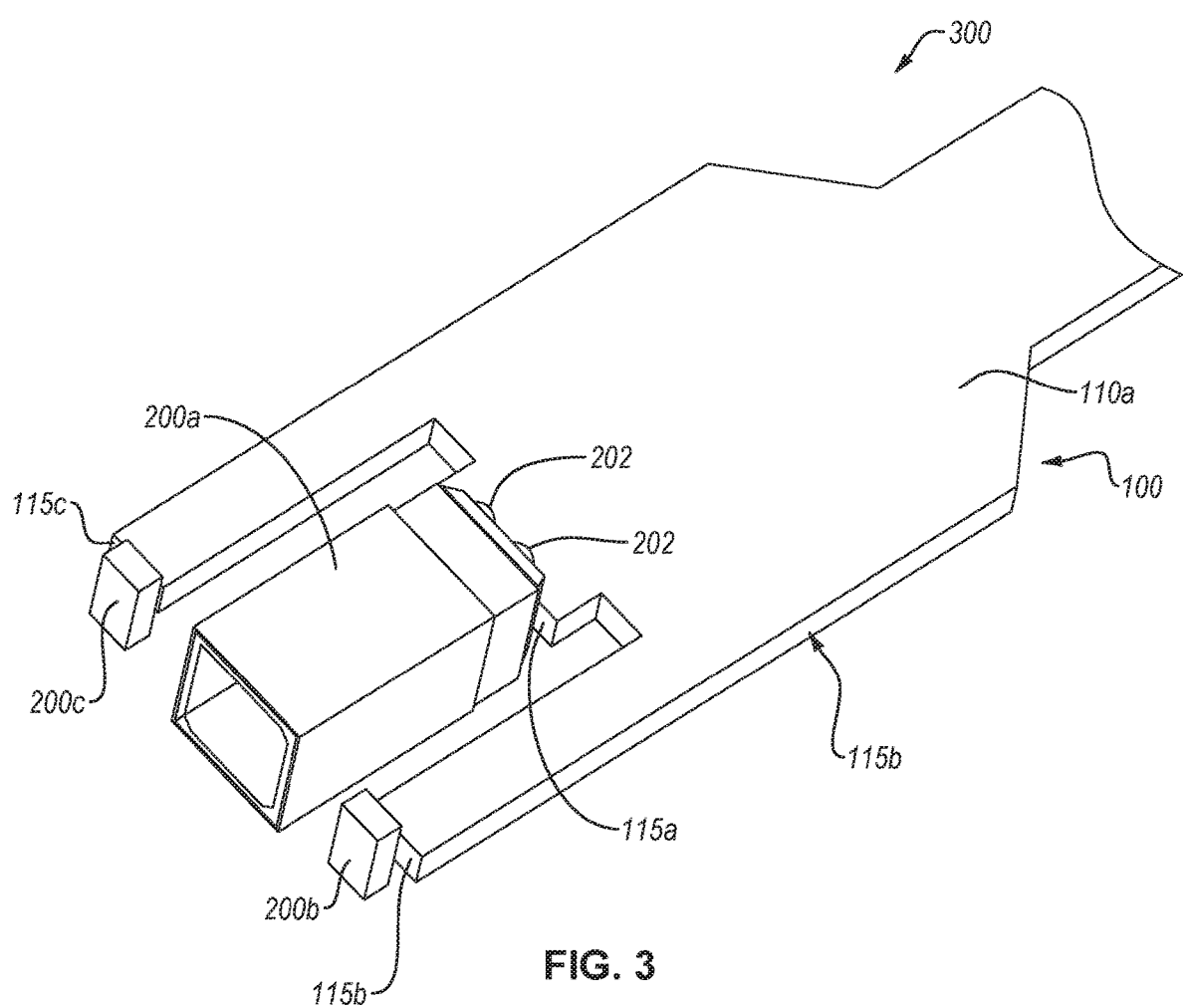
FIG. 3 illustrates a perspective view of electronic components end mounted to a printed circuit board, according to one or more examples of the present disclosure.
Figure 4:
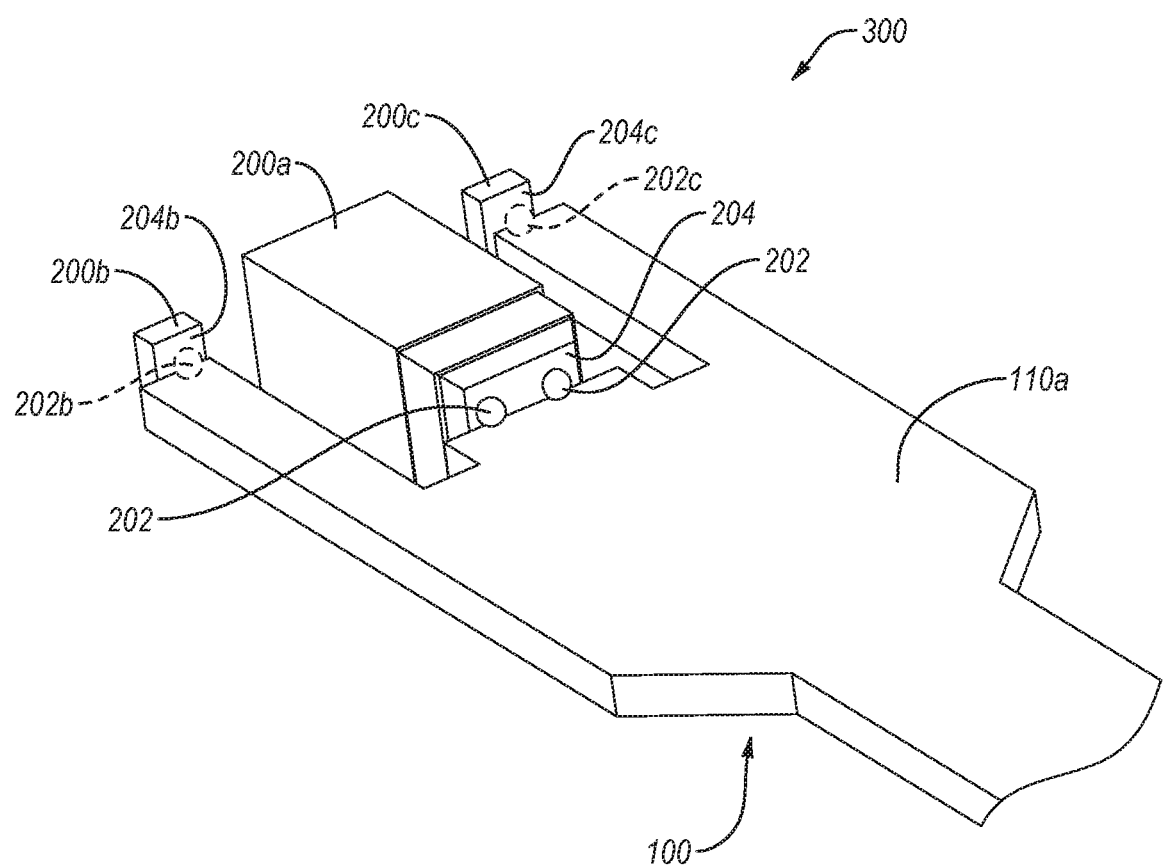
FIG. 4 illustrates a perspective view of electronic components end mounted to a printed circuit board, according to one or more examples of the present disclosure.

Referring now to FIGS. 3 and 4, perspective views of an apparatus 300 utilizing an end mount (i.e., edge mount) technique to end mount electronic components to a printed circuit board 100 are shown. The electronic components can be any of various electronic components and the printed circuit board 100 can be a flexible printed circuit board. As described more fully below, an end mount, as defined herein, is a mounting of an electronic component to a minor surface 115 or edge of the circuit board 100, such that the electronic component overhangs the minor surface 115. As shown, the circuit board 100 includes a top major surface 110a and a bottom major surface 110b (not visible in FIGS. 3 and 4). The circuit board 100 also includes a plurality of minor surfaces 115, including three minor surfaces 115a-115c to which an electronic component is end mounted. In some examples, the printed circuit board 100 is flexible, semi-rigid, or rigid. A semi-rigid circuit board is a flexible circuit board with an embedded stiffener spanning at least a portion of the flexible circuit board.

A first electronic component 200a is end mounted to, and overhangs, a first minor surface 115a of the circuit board 100. A second electronic component 200b is end mounted to, and overhangs, a second minor surface 115b of the circuit board 100. A third electronic component 200c is end mounted to, and overhangs, a third minor surface 115c of the circuit board 100. As shown in FIGS. 3 and 4, the first electronic component 200a includes solder balls 202 on a connecting surface 204 of the first electronic component 200a.

The first electronic component 200a is end mounted to the circuit board 100 such that the connecting surface 204 is orthogonal to the top major surface 110a and the bottom major surface of the circuit board 100. In some embodiments, the minor surface 115a of the circuit board 100 is positioned between at least two solder balls 202 (e.g., at least one solder ball 202 on each side of the minor surface 115a or two rows of at least two solder balls 202 in the illustrated example) on the first electronic component 200a. As can be seen in FIG. 3 and more clearly in FIG. 4, at least one (e.g., two) of the four solder balls 202 of the first electronic component 200a are above the top major surface 110a. Although not visible, the remaining one or more solder balls 202 of the first electronic component 200a are below the bottom major surface of the circuit board 100. The solder balls 202 may be described as straddling the circuit board 100 across a thickness of the circuit board 100.

In some embodiments, the first electronic component 200a is electrically connected (e.g., soldered, welded, brazed, connectorized, conductive epoxied, etc.) to both the top major surface 110a and the bottom major surface of the circuit board 100. As shown, the top major surface 110a and the bottom major surface are parallel opposite sides of the circuit board 100. The first electronic component 200a is electrically connected to both major surfaces 110 from a single mounting surface 204.

The apparatus 300 also includes a second electronic component 200b which is end mounted to the second minor surface 115b of the circuit board 100. The second electronic component 200b is coupled to the circuit board 100 in a similar manner to the manner described in conjunction with the first electronic component 200a. The second electronic component 200b is coupled to the circuit board 100 such that a single mounting surface 204b of the second electrical component 200b is orthogonal to the top major surface 110a and the bottom major surface 110b of the circuit board 100. Although coupled to the circuit board 100 with solder fillets 302 in most examples (see, e.g., FIG. 7), in some examples, when BGA style components are used, the second minor surface 115b of the circuit board 100 is positioned between solder balls 202b of the second electronic component 200b. The second electronic component 200b is electrically connected to both the top major surface 110a and the bottom major surface of the circuit board 100 by the single mounting surface 204b. For some second electrical components 200b having multiple (e.g., four) possible mounting surfaces and mounting orientations, regardless of which one of the mounting surfaces is mounted to the minor surface 115b of the circuit board 100, that mounting surface is perpendicular to the major surfaces of the circuit board 100.

The apparatus 300 also includes a third electronic component 200c which is end mounted to the third minor surface 115c of the circuit board 100. The third electronic component 200c is coupled to the circuit board 100 in a similar manner to the manner described in conjunction with the first electronic component 200a. The third electronic component 200c is coupled to the circuit board 100 such that a single mounting surface 204c of the third electronic component 200c is orthogonal to the top major surface 110a and the bottom major surface 110b of the circuit board 100. Although coupled to the circuit board 100 with solder fillets 302 in most examples (see, e.g., FIG. 7), in some examples, when BGA style components are used, the third minor surface 115c of the circuit board 100 is positioned between solder balls 202c of the third electronic component 200c. The third electronic component 200c is electrically connected to both the top major surface 110a and the bottom major surface of the circuit board 100 by the single mounting surface 204c. For some third electrical components 200c having multiple (e.g., four) possible mounting surfaces and mounting orientations, regardless of which one of the mounting surfaces is mounted to the minor surface 115c of the circuit board 100, that mounting surface is perpendicular to the major surfaces of the circuit board 100.

End mounts, as described in conjunction with FIG. 3, allow for a lower vertical profile of the apparatus 300. That is, if the electronic components are coupled to a major surface 110 of the circuit board 100, the vertical profile (measured in a direction orthogonal to the major surfaces 100) is much greater than if the electronic components are end mounted to the minor surfaces 115 as described herein.

Figure 5:
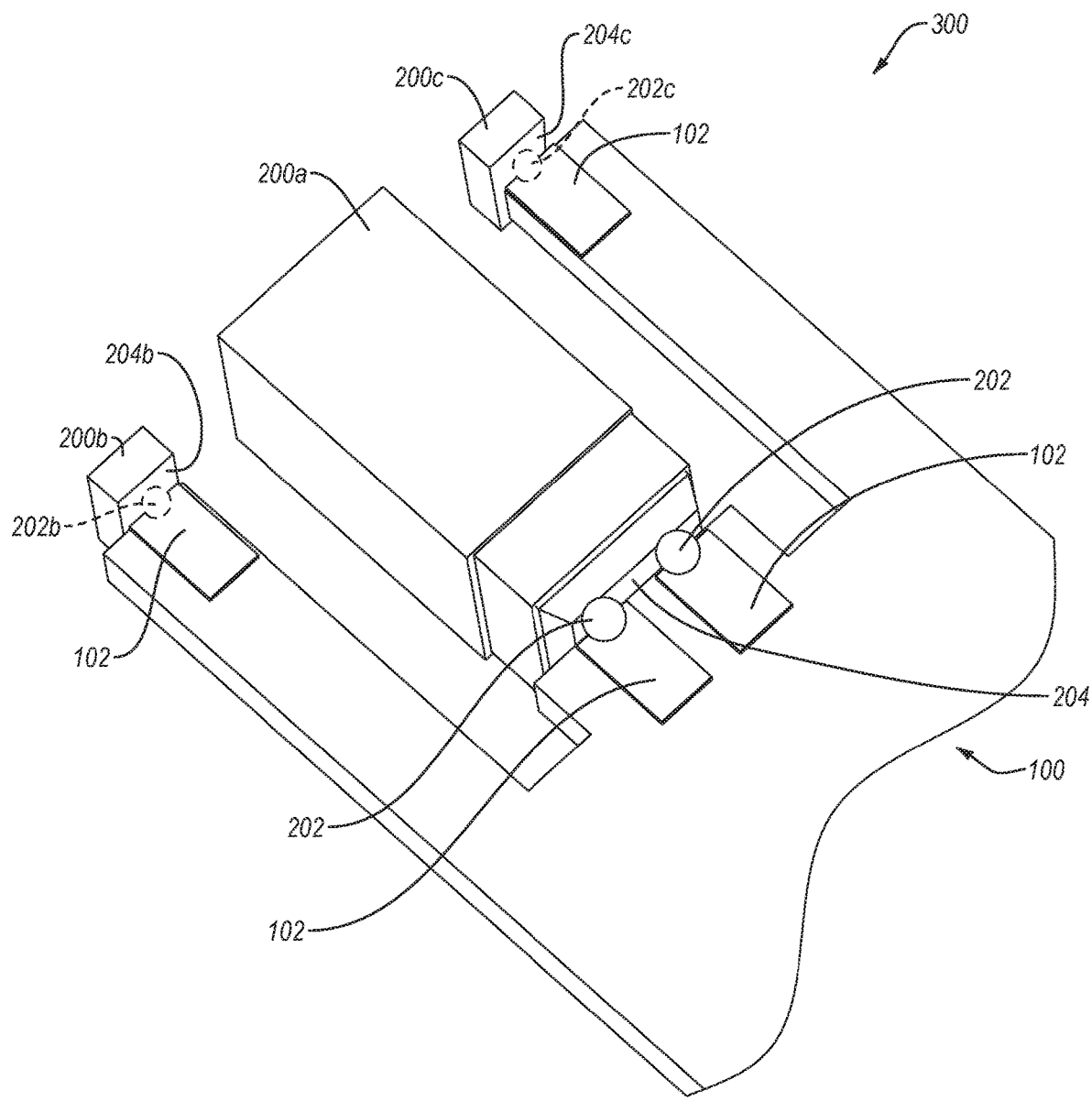
FIG. 5 illustrates a perspective view of electronic components end mounted to a printed circuit board, according to one or more examples of the present disclosure.
Figure 6:
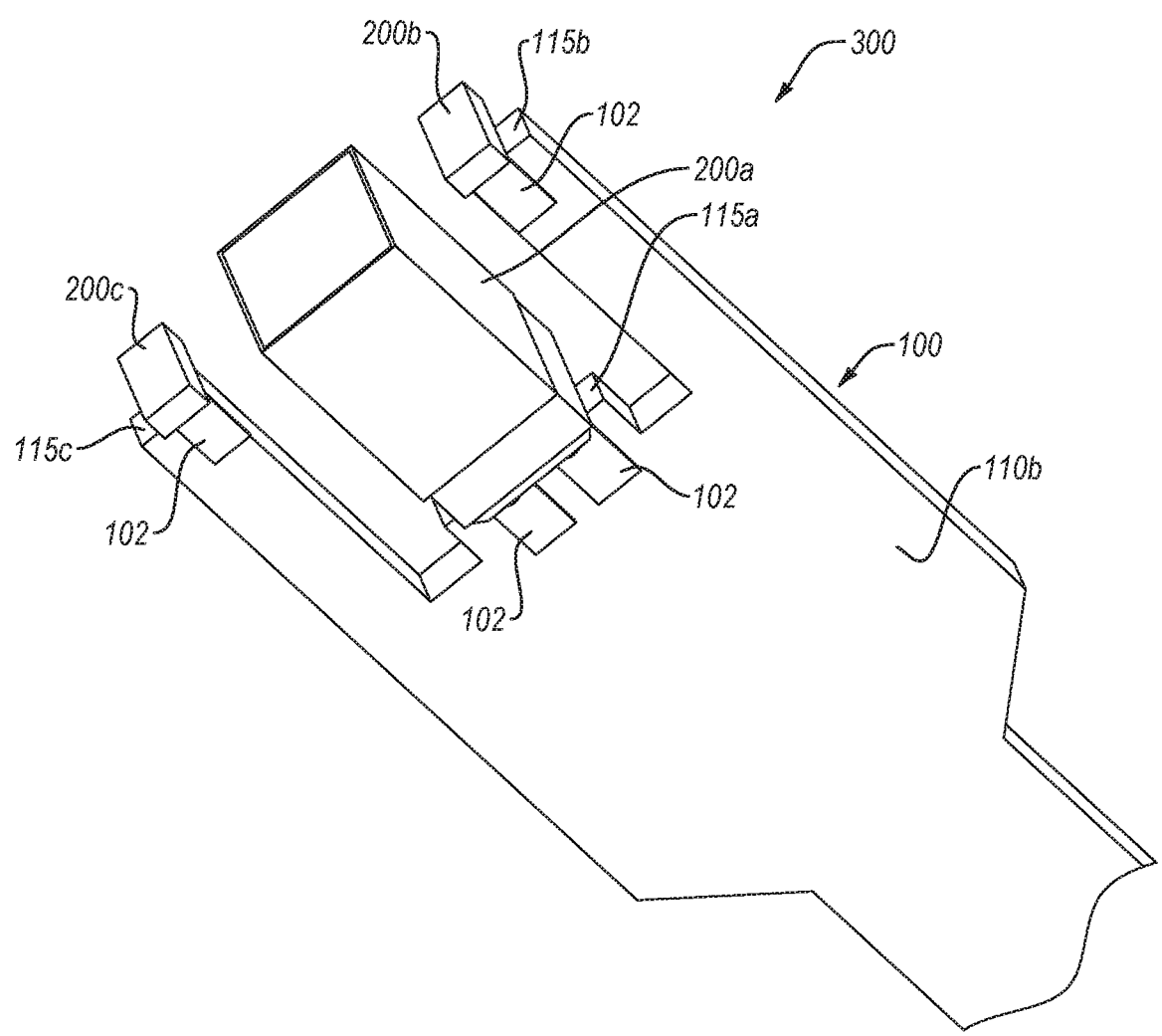
FIG. 6 illustrates a perspective view of electronic components end mounted to a printed circuit board, according to one or more examples of the present disclosure.

Referring now to FIGS. 5 and 6, perspective views of an apparatus 300 utilizing an end mounting technique to end mount electronic components to a printed circuit board 100 are shown. The apparatus 300 is similar to and may include some or all the features described in conjunction with the apparatus 300 of FIGS. 3 and 4. The printed circuit board 100 includes various pads 102 visible on the top major surface 110a of the printed circuit board 100. The pads 102 are near or adjacent to the minor surfaces 115 of the printed circuit board 100. The solder balls 202 of the electronic components may be electrically connected or soldered to the pads 102 of the printed circuit board 100 using SMT techniques or any of various other techniques, such as through the use of soldering irons or hot air, or via a robotic assembly that dispenses solder paste and activates the solder past using a laser, one or more of such techniques are described in more detail below.

Referring to FIG. 6, the bottom major surface 110b is shown with various pads 102 visible. The pads 102 are near or adjacent to the minor surfaces 115 of the printed circuit board 100. The solder balls 202 of the electronic components may be electrically connected or soldered to the pads 102 of the printed circuit board 100.

Figure 7:
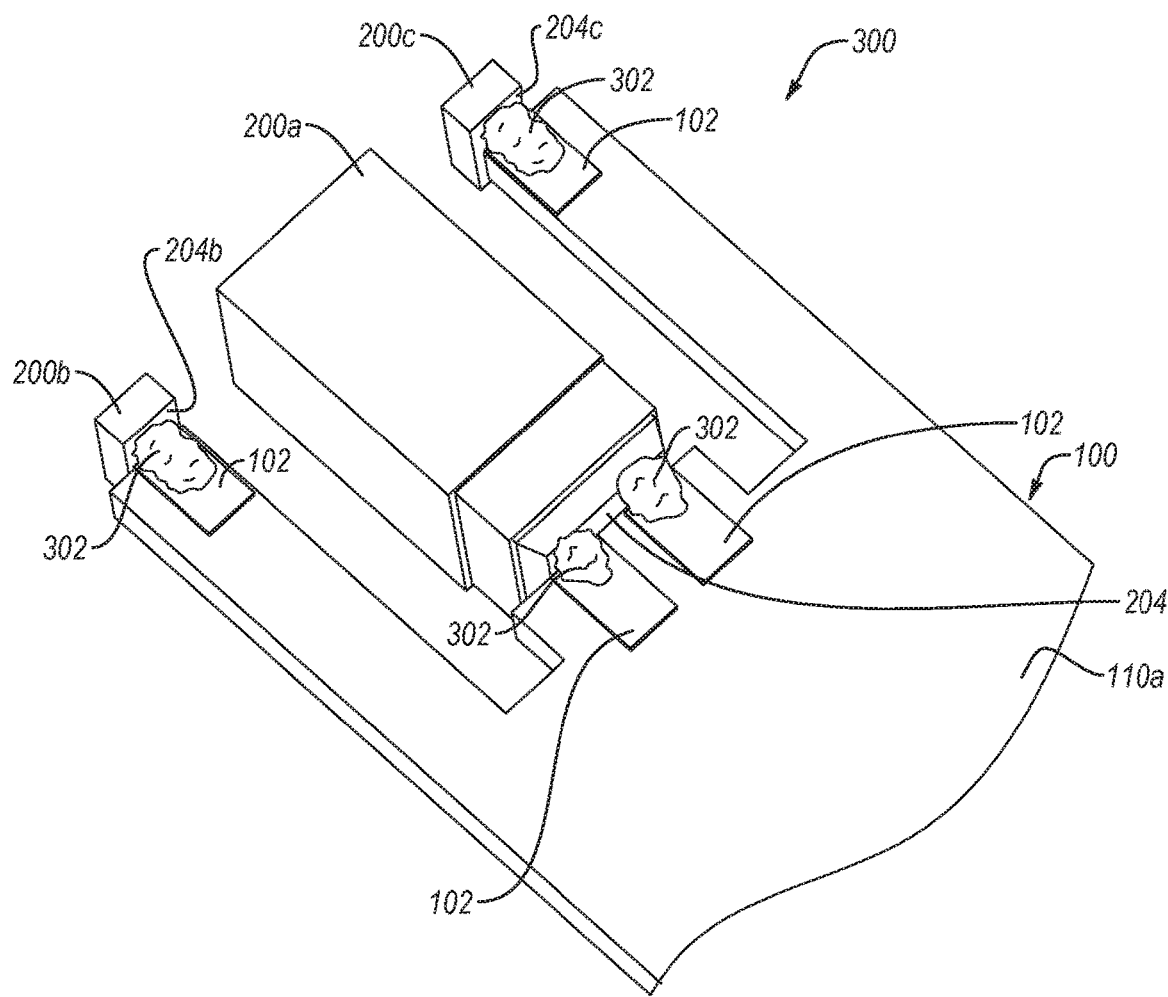
FIG. 7 illustrates a perspective view of electronic components end mounted to a printed circuit board with the solder connections, according to one or more examples of the present disclosure.
Figure 8:
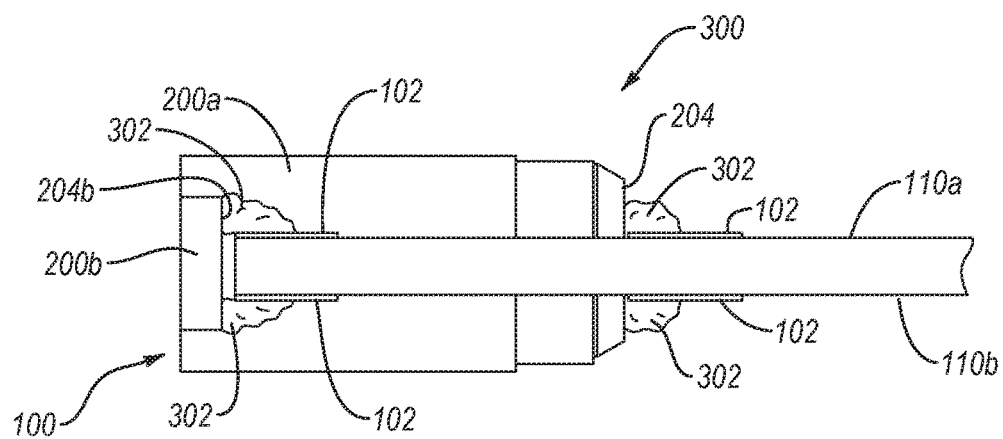
FIG. 8 illustrates a side view of electronic components end mounted to a printed circuit board with the solder connections, according to one or more examples of the present disclosure.

Referring now to FIGS. 7 and 8, a perspective view and a side view, respectively, of an apparatus 300 are shown. The electronic components are electrically connected to the printed circuit board 100 by solder fillets 302. As can be seen more clearly in FIG. 8, the electronic components are connected to the printed circuit board 100 on both the top major surface 110a and the bottom major surface 110b of the printed circuit board 100. The apparatus 300 includes solder fillets 302 on each side of the minor surfaces 115 to provide stability to the electronic components 200. In some examples, the solder fillets 302 used to solder the first electrical component 100a to the circuit board 100 is a solder paste with a reflow temperature of no more than 175° C. Such a solder paste helps to reduce damage to (e.g., melting, warping, distortion or) the solder balls 202, such as delamination from the connecting surface 204. In some examples, the solder paste of the solder fillets 302 used to solder the first electrical component 100a to the circuit board 100 includes a collection of small solder particles (e.g., spheres).

Figure 9:
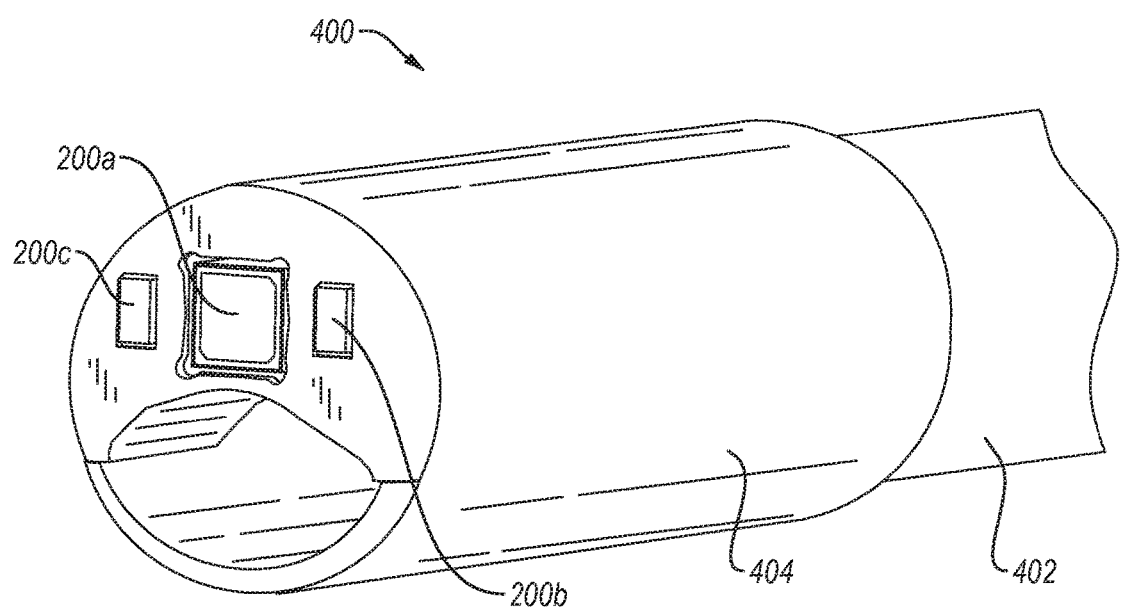
FIG. 9 illustrates a perspective view of a scope utilizing electronic components end mounted to a printed circuit board, according to one or more examples of the present disclosure.
Figure 10:
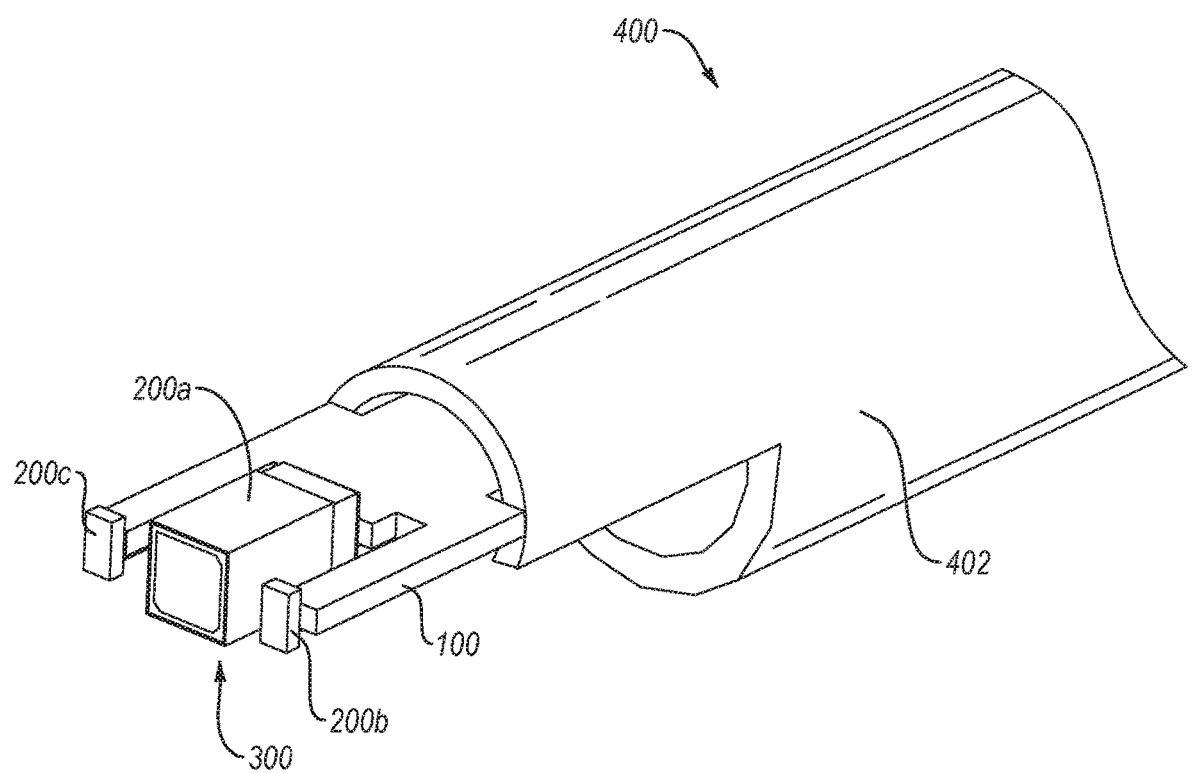
FIG. 10 illustrates a perspective view of the scope of FIG. 9 with the tip housing removed, according to one or more examples of the present disclosure.

Referring now to FIGS. 9 and 10, an implementation of an apparatus 300 is shown. The apparatus 300 includes some or all of the features described in conjunction with FIGS. 3-8. FIG. 9 illustrates a perspective view of a scope 400. FIG. 10 illustrates a perspective view of the scope 400 with a tip housing 404 removed to show the apparatus 300.

The apparatus 300 may be utilized in many applications that require a reduction in size or a lower profile and may include, but is not limited to, bore scopes, medical imaging (endoscopes, hysteroscopes, otoscopes, laparoscopes, gastroscopes, bronchoscopes, cystoscopes, ureteroscopes, arthroscopes, colonoscopes), catheters, needles, and other similar applications. Many applications utilize a flexible tube or probe and as such the printed circuit board 100 is flexible and allows for the flexible tube or probe to be maneuvered in tight spaces. Reduction in size of the profile of the apparatus 300 allow for utilization of electronic components with smaller scopes and catheters.

In an implementation, the first electronic component 200a is a camera and the second and third electronic components 200b, 200c are light sources, typically LEDs. As shown in FIG. 9, the electronic components 200a, 200b, 200c are exposed through apertures in the tip housing 404 and provide function to the scope 400.

Embodiments described herein may include end mounting of any of various electronic components to an edge of a printed circuit board where the electronic component was originally designed for SMT mounting to a major surface of a printed circuit board.

Figure 11:
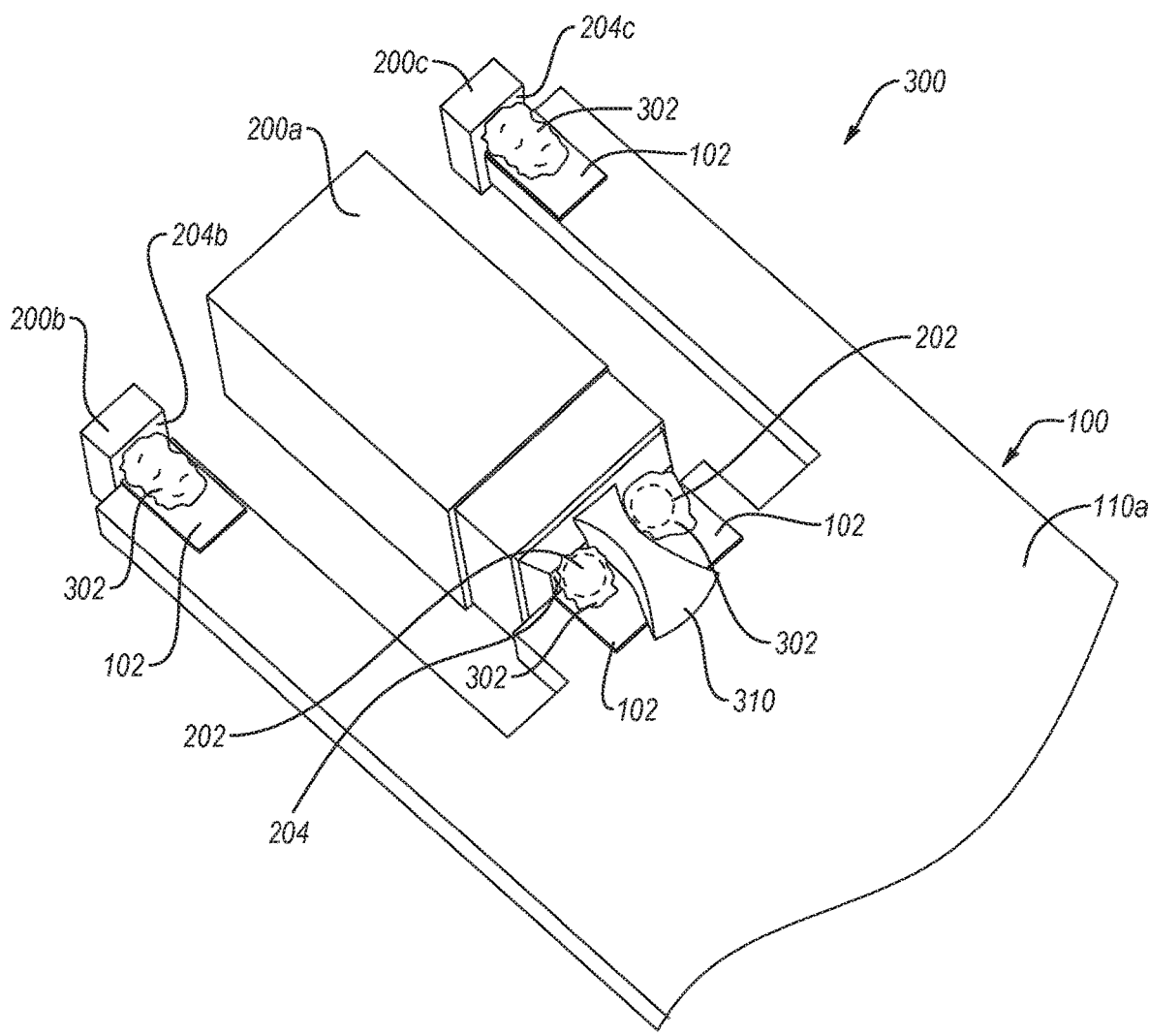
FIG. 11 illustrates a perspective view of electronic components end mounted to a printed circuit board, according to one or more examples of the present disclosure.
Figure 12:
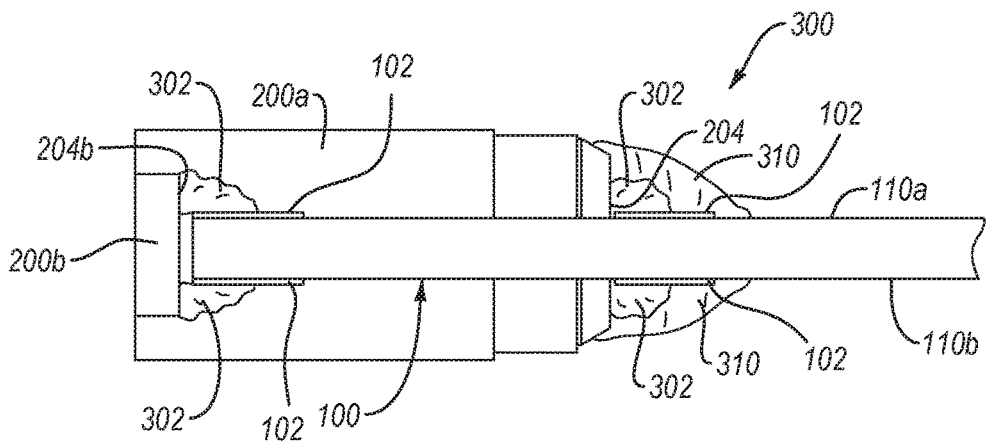
FIG. 12 illustrates a side elevation view of electronic components end mounted to a printed circuit board, according to one or more examples of the present disclosure.

Referring to FIGS. 11 and 12, according to yet another example, the apparatus 300 includes a gusset 310 on the top major surface 110a of the circuit board 100 and a gusset 310 on the bottom major surface 110B of the circuit board 100. The gussets 310 are further coupled to the connecting surface 204 of the first electronic component 200a. Accordingly, a first one of the gussets 310 extends from the top major surface 110a of the circuit board 100 to the connecting surface 204 of the first electronic component 200a, and a second one of the gussets 310 extends from the bottom major surface 110b of the circuit board 100 to the connecting surface 204 of the first electronic component 200a. Each one of the gussets 310 is narrow enough to be located between the solder fillets 302 of the first electronic component 200a on the corresponding side of the circuit board 100. In other words, in certain examples, each one of the gussets 310 is interposed between, but does not cover or overlay, the solder fillets 302 of the first electronic component 200a on the corresponding side of the circuit board 100.

The gussets 310 help to transfer mechanical loads from the first electronic component 200a to the circuit board 100. For example, in the implementations where the first electronic component 200a is a camera, and thus a relatively large electronic component relative to the circuit board 100, the gussets 310 help to relieve the strain placed on the camera during use, which helps to maintain a strong mechanical and electrical connection between the camera and the circuit board 100.

The gussets 310 can be made from any of various materials and have any of various shapes that allow for the separation of the major surfaces of the circuit board 100 and that help transfer mechanical loads. According to certain examples, the gussets 310 are made of a hardened or cured epoxy material. The epoxy material of the gussets 310 can be a thermoset or a thermoplastic material. In some examples, the gussets 310 are deposited in place, between the first electronic component 200a and the respective major surfaces of the circuit board 100, in a flowable or molten state and then allowed to harden, either by the application of heat, in the case of a thermoset material, or a cooling process, in the case of a thermoplastic material. In certain examples, the epoxy material of the gussets 310 are applied and hardened before the solder fillets 302 are applied. However, in other examples, the epoxy material of the gussets 310 are applied and hardened after the solder fillets 302 are applied. The epoxy material can be a UV or heat cured epoxy, that hardens relative quickly, or a 2-part epoxy that hardens over time.

Figure 13:
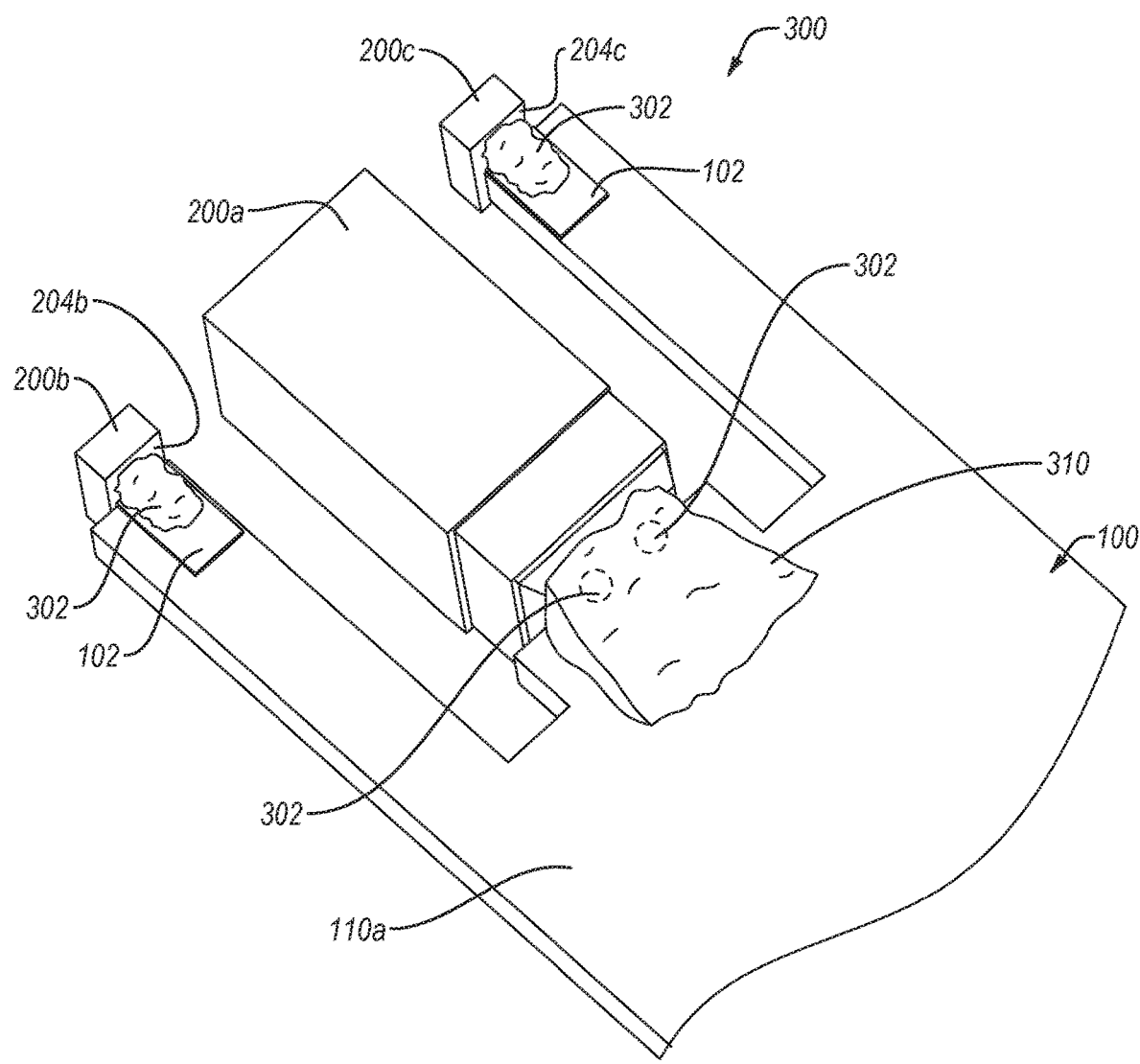
FIG. 13 illustrates a perspective view of electronic components end mounted to a printed circuit board, according to one or more examples of the present disclosure.

As shown in FIG. 13, according to other examples, instead of locating the gussets 310 just between the corresponding solder fillets 302, as with the apparatus 300 of FIGS. 11 and 12, the solder fillets 302 of the apparatus 300 of FIG. 13 are at least partially covered by the gussets 310. In some examples, as depicted, the corresponding solder fillets 302 (shown in hidden line) are completely covered by the gussets 310. Such a configuration provides additional relief from strain applied to the first electronic component 200a, and promotes the durability of the solder fillets 302. In these examples, the solder fillets 302 are applied or deposited first before the gussets 310 are applied or deposited.

Figure 14:
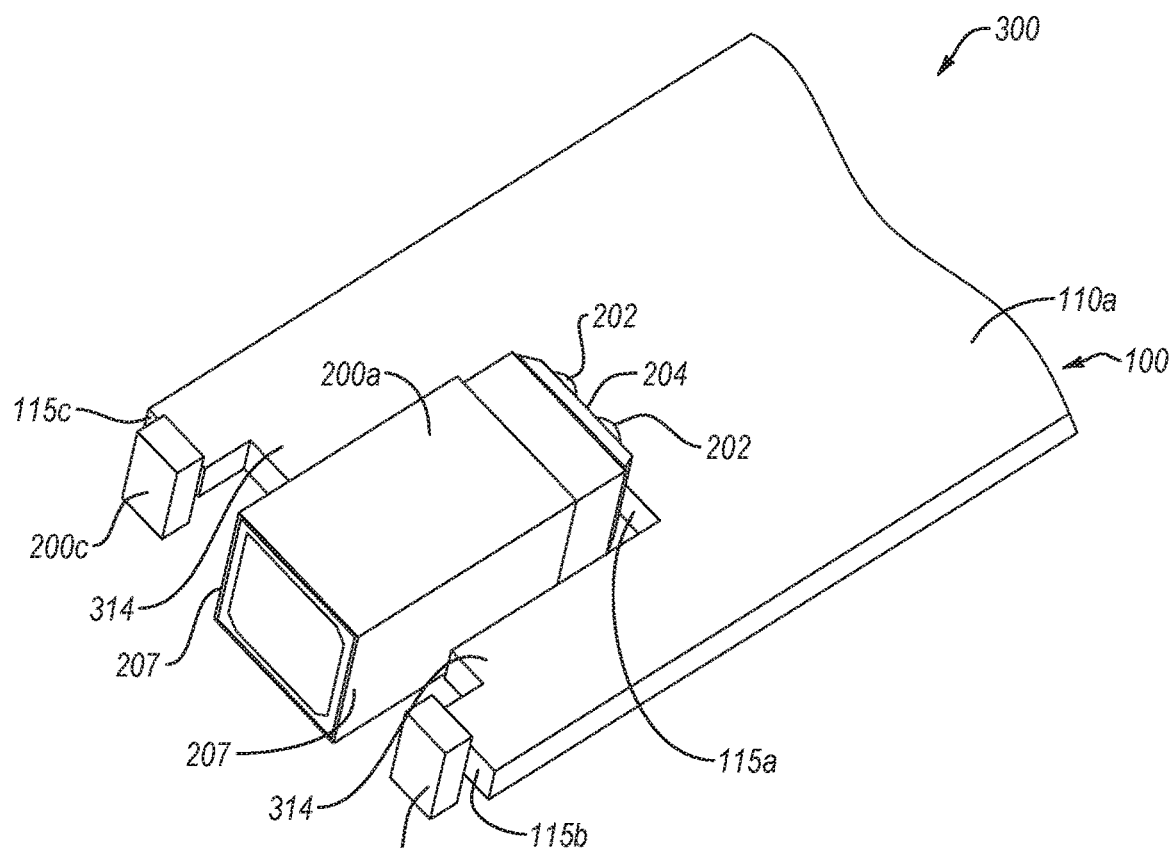
FIG. 14 illustrates a perspective view of electronic components in preparation to be end mounted to a printed circuit board, according to one or more examples of the present disclosure.
Figure 15:
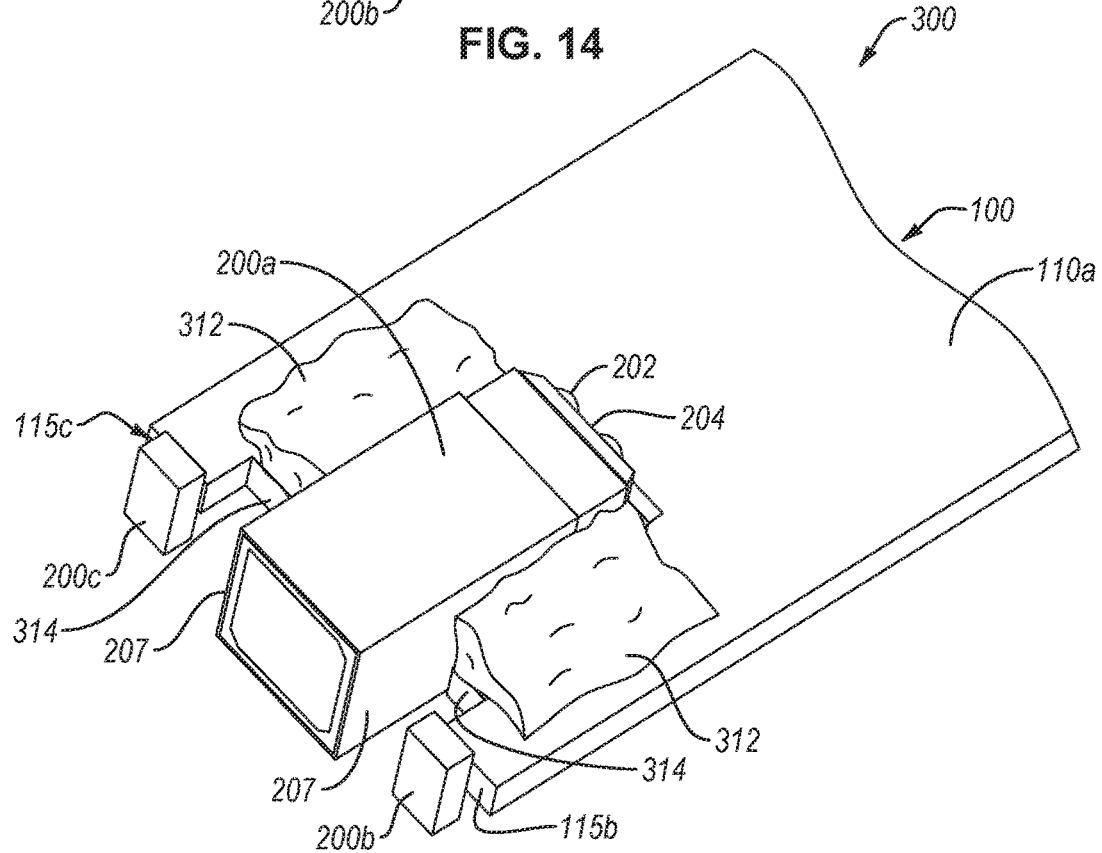
FIG. 15 illustrates a perspective view of electronic components end mounted to a printed circuit board, according to one or more examples of the present disclosure.

Referring to FIGS. 14 and 15, according to certain examples, the circuit board 100 of the apparatus 300 is reshaped to provide a tighter fit along opposing sides of the first electronic component 200a. Accordingly, in some examples, in addition to the connecting surface 204 being in contact with an edge of the circuit board 100, opposing sides 207 of the first electronic component 200a, which extend at an angle (e.g., 90-degrees) relative to the connecting surface 204 are also in contact with respective edges of the circuit board 100 defined by respective extension portions 314. The extension portions 314 effectively fill in the gap between the sides 207 of the first electronic component 200a and the circuit board 100 (see, e.g., FIG. 13).

Additionally, the apparatus 300 in FIGS. 14 and 15 includes gussets 312 on the top major surface 110a of the circuit board 100 and gussets 312 on the bottom major surface 110B of the circuit board 100. The gussets 312 on each major surface of the circuit board 100 are further coupled to corresponding ones of the opposing sides 207 of the first electronic component 200a in contact with the extension portions 314 of the circuit board 100. Accordingly, a first one of the gussets 312 extends from the top major surface 110a of the circuit board 100 to a first side 207 of the first electronic component 200a, and a second one of the gussets 312 extends from the top major surface 110a of the circuit board 100 to a second side 207 of the first electronic component 200a. Likewise, although not shown, a third one of the gussets 312 extends from the bottom major surface 110b of the circuit board 100 to the first side 207 of the first electronic component 200a, and a fourth one of the gussets 312 extends from the bottom major surface 110b of the circuit board 100 to the second side 207 of the first electronic component 200a. In some examples, the circuit board 100, while not in physical contact with the opposing sides 207 of the first electronic component 200a, is in close enough proximity to the circuit board 100 to enable gussets 310 to extend from the major surfaces of the circuit board 100 to the opposing sides 207 of the first electronic component 200a.

In some examples, the apparatus 300 of FIGS. 14 and 15 additionally includes gussets 310 at the connecting surface 204 of the first electronic component 200a, in the same manner as described above in association with the apparatus 300 of FIGS. 11 and 12 or the apparatus 300 of FIG. 13. However, in other examples, to simplify the manufacturing process, the apparatus 300 of FIGS. 14 and 15 does not include gussets 310 at the connecting surface 204.

Figure 16:
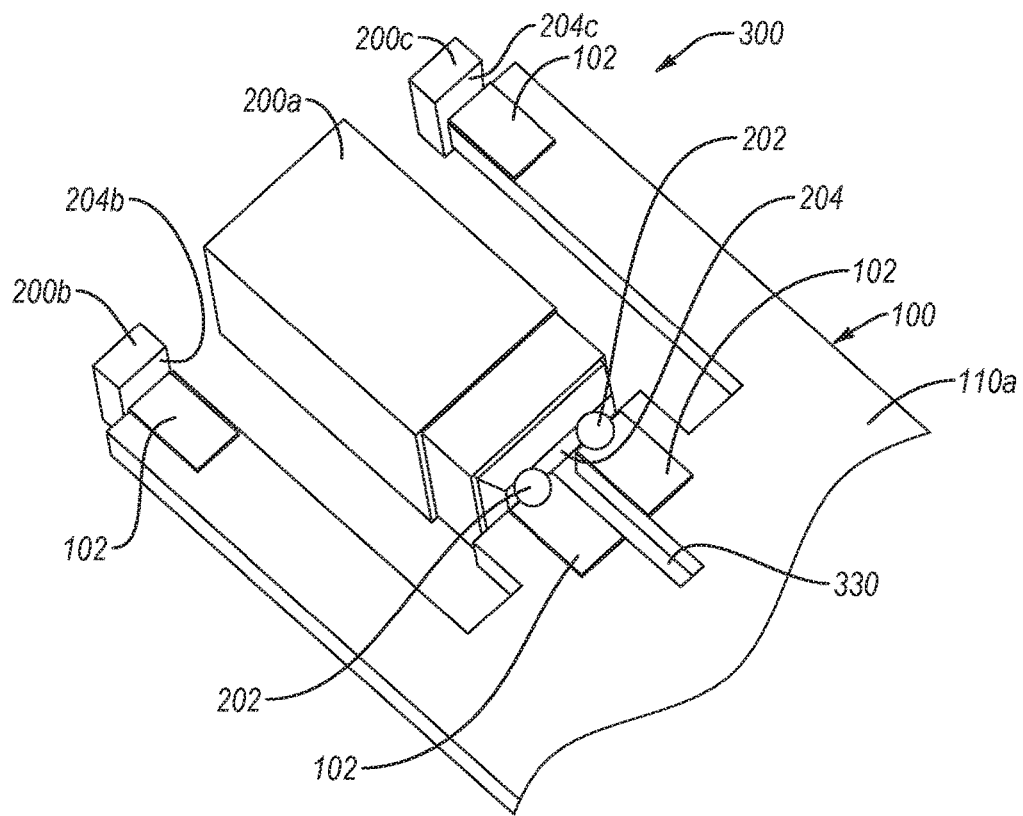
FIG. 16 illustrates a perspective view of electronic components in preparation to be end mounted to a printed circuit board, according to one or more examples of the present disclosure.
Figure 17:
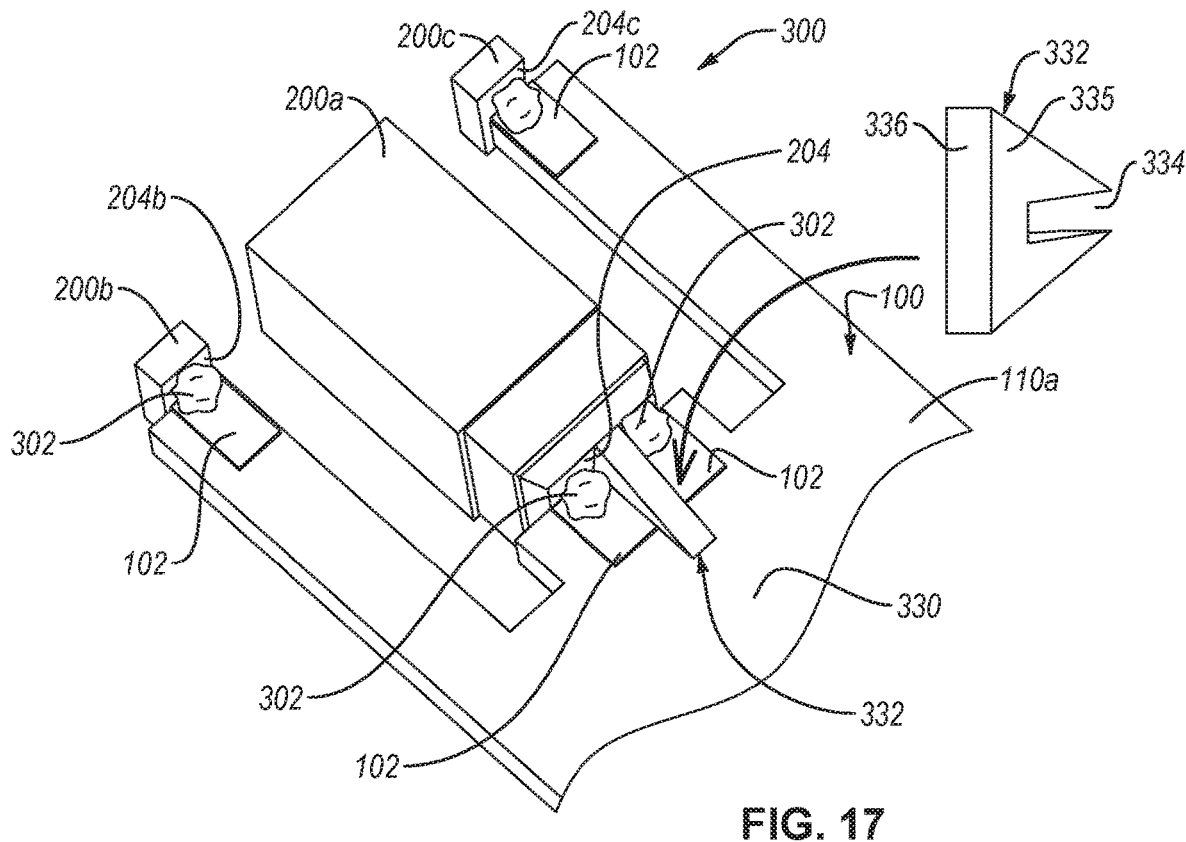
FIG. 17 illustrates a perspective view of electronic components end mounted to a printed circuit board, according to one or more examples of the present disclosure.

Referring now to FIGS. 16 and 17, according to certain examples, instead of or in addition to using the gussets 310 and/or the gussets 312 to help stabilize the first electronic component 200a, the apparatus 300 utilizes a support bracket 332. The support bracket 332 is a pre-formed component configured to mechanically couple together the circuit board 100 and the first electronic component 200a. As shown in FIG. 16, the circuit board 100 further includes a slot 330 formed in and extending from the minor surface 115a of the circuit board 100 to which the first electronic component 200a is end mounted (e.g., the minor surface 115a). In certain examples, as shown, the slot 330 is interposed between the pads 102 to which the solder balls 202 of the first electronic component 200a are soldered.

The support bracket 332 is made of a rigid materials, such as a hardened plastic. In some examples, the support bracket 332 is more rigid than the circuit board 100. The support bracket 332 includes a second slot 334 that is configured to receive a portion of the circuit board 100 therein. The support bracket 332 additionally includes an engagement surface 336 that is configured to contact and supportably engage the connecting surface 204 of the first electronic component 200a. A top portion of the support bracket 332 extends from the top major surface 110a of the circuit board 100 to the connecting surface 204 of the first electronic component 200a, and a bottom portion of the support bracket 332 extends from the bottom major surface 110b of the circuit board 100 to the connecting surface 204 of the first electronic component 200a. In some implementations, the engagement surface 336 is shaped to sit flush against the connecting surface 204. For example, the engagement surface 336 can be flat. The second slot 334 is spaced apart from the engagement surface 336 by an intermediate portion 335 of the support bracket 332. To help promote a streamlined shape and reduce the profile of the apparatus 300, in some examples, the support bracket 332 tapers from the engagement surface 336 towards the second slot 334. In certain examples, the support bracket 332 tapers to a knife edge. However, the support bracket 332 can have any of various shapes that allow for the separation of the major surfaces of the circuit board 100 and that help transfer mechanical loads.

The apparatus 300 of FIG. 17 is assembled by sliding the support bracket 332 into and along the slot 330 of the circuit board 100 until the circuit board 100 is slidably and fully received within the second slot 334 of the support bracket 332. The circuit board 100 is fully received within the second slot 334 when an end of the slot 330 contacts an end of the second slot 334. The length of the slot 330 and the length of the intermediate portion 335 of the support bracket 332 are the same in some examples, such that when the circuit board 100 is fully received within the second slot 334, the engagement surface 336 sits flush with the minor surface of the circuit board 100 to which the first electronic component 200a is end mounted. In this manner, when the first electronic component 200a is subsequently end mounted to the minor surface 115a of the circuit board 100 with the solder fillets 302, the engagement surface 336 is positioned to contact and support the connecting surface 204 of the first electronic component 200a. In other words, the support bracket 332 is coupled to the circuit board 100 first and then the first electronic component 200a is end mounted to the circuit board 100 with the support bracket 332 in place. In certain examples, the engagement surface 336 is bonded to the connecting surface 204 with a suitable adhesive to further optimize the structural integrity of the mechanical support.

As shown, the engagement surface 336 is elongated in a first direction, which is perpendicular to the minor surface 115a of the circuit board, such that the engagement surface 336 extends along and supports the connecting surface 204 in a first direction and the minor surface 115a extends along and supports the connecting surface 204 in a second direction, perpendicular to the first direction. Accordingly, in some examples, the bracket 332 is perpendicular to the circuit board 100 when supporting the first electronic component 200a. Such a configuration promotes a stable coupling between the first electronic component 200a and the circuit board 100.

Figure 18:
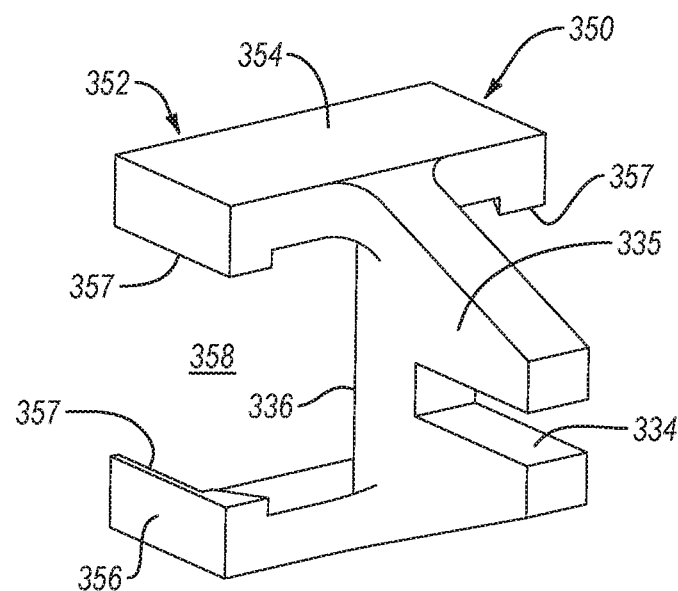
FIG. 18 illustrates a perspective view of a support bracket, according to one or more examples of the present disclosure.
Figure 19:
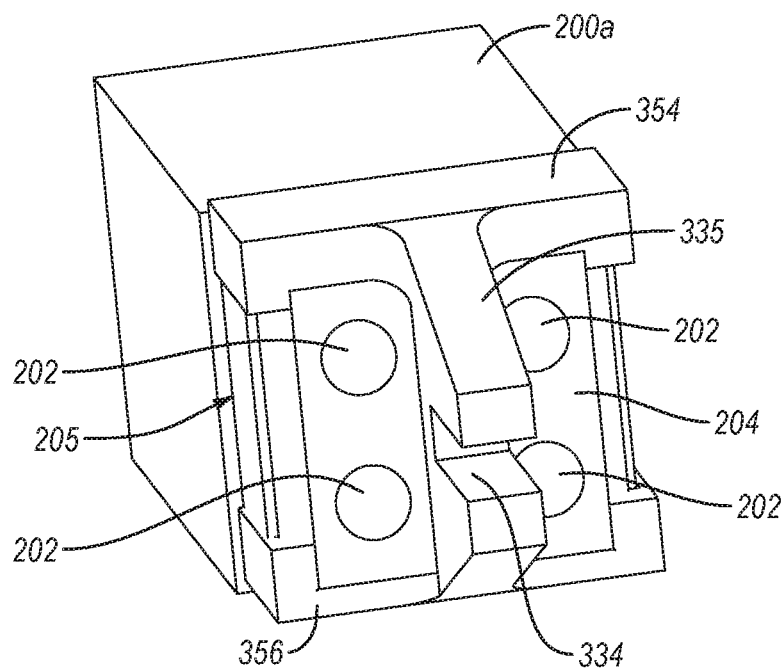
FIG. 19 illustrates a perspective view of a support bracket coupled to an electronic component, according to one or more examples of the present disclosure.

Referring to FIGS. 18 and 19, another example of the apparatus 300 includes a support bracket 350 that is more robust than the support bracket 332 of the apparatus 300 of FIGS. 16 and 17. The support bracket 350, like the support bracket 332, includes a second slot 334, an engagement surface 336, and an intermediate portion 336 interposed between the engagement surface 336 and the second slot 334. The support bracket 350 also tapers from the engagement surface 336 towards the second slot 334. Similar to the support bracket 332, the support bracket 350 is configured to fully slidably receive the circuit board 100 into the second slot 334 such that the engagement surface 336 sits flush with the minor surface of the circuit board 100 to which the first electronic component 200a is end mounted.

However, unlike the support bracket 332, the support bracket 350 includes a supplemental engagement portion 352 extending from the engagement surface 336 away from the slot 334. The supplemental engagement portion 352 includes a first flange 354 and a second flange 356. The first flange 354 and the second flange 356 are spaced apart from each other such that the engagement surface 336 extends between the first flange 354 and the second flange 356. In certain examples, the first flange 354 and the second flange 356 are substantially parallel to each other. Moreover, in some examples each one of the first flange 354 and the second flange 356 includes opposing overhang tabs 357 that extend towards the opposing overhang tabs 357 of the other one of the first flange 354 and the second flange 356. The space between the first flange 354 and the second flange 356 defines a component receptacle 358 sized to matingly receive a connecting end portion 205 of the first electronic component 200a. The connecting end portion 205 of the first electronic component 200a includes the connecting surface 204 and may have an outer peripheral shape that is different than the rest of the first electronic component 200a.

Referring to FIG. 19, the connecting end portion 205 is shown inserted into the component receptacle 358 of the support bracket 350. When inserted into the component receptacle 358, the first flange 354 and the second flange 356 engage opposing sides of the connecting end portion 205 to support the first electronic component 200a and limit movement of the first electronic component 200a in first directions. Additionally, the opposing overhang tabs of the first flange 354 and the second flange 356 also engage opposing sides of the connecting end portion 205 to support the first electronic component 200a and limit movement of the first electronic component 200a in second directions perpendicular to the first directions. In this manner, the supplemental engagement portion 352 at least partially wraps around or encircles the connecting end portion 205, to provide stability to the first electronic component 200a in addition to that provided by the engagement surface 336, when the first electronic component 200a is end mounted to the circuit board 100. As shown in FIG. 19, the supplemental engagement portion 352 is specifically configured extend around the solder balls 202 so as not to obstruct the soldering of the solder balls 202 to the circuit board 100.

Figure 20:
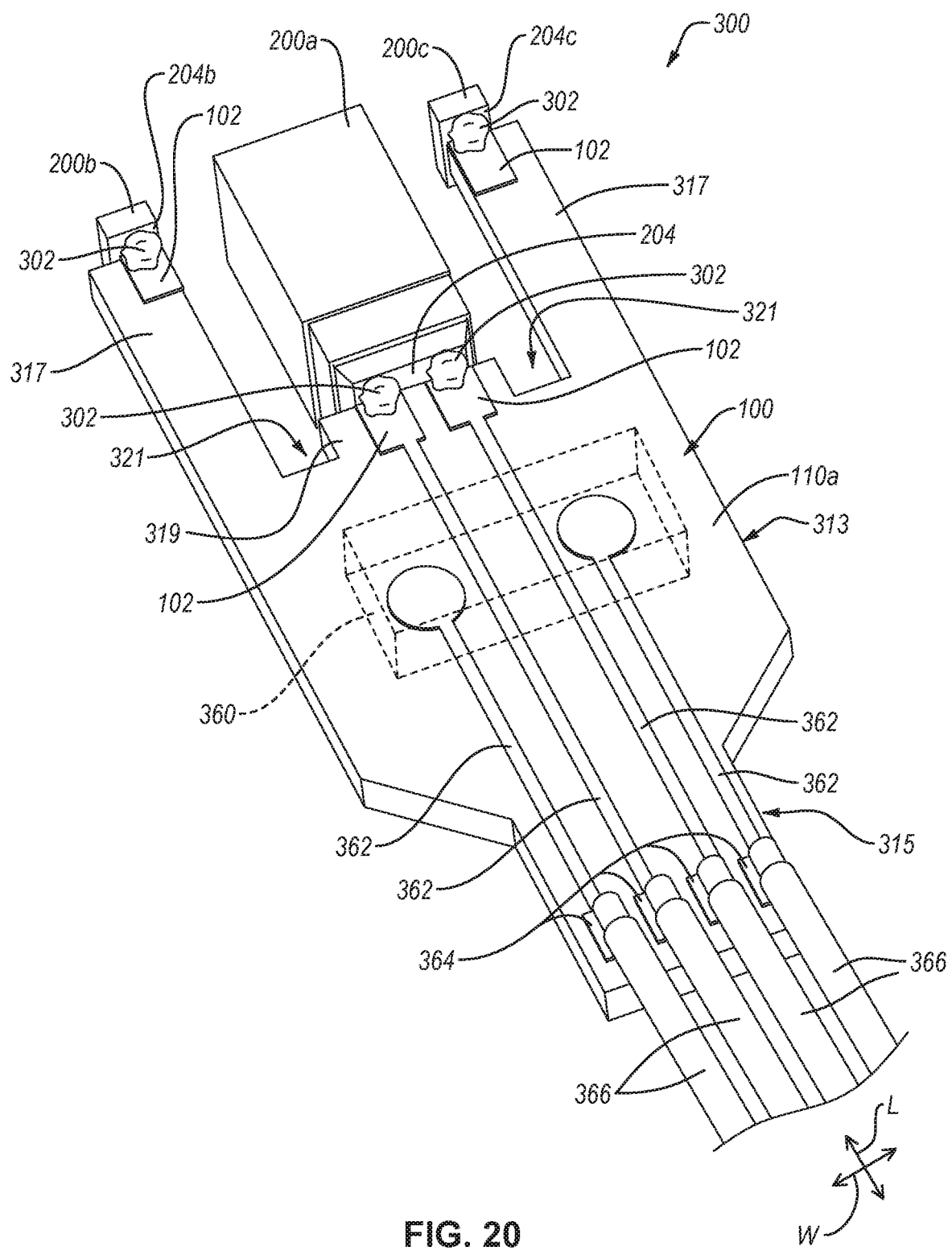
FIG. 20 illustrates a perspective view of an electronic component end mounted to a printed circuit board, according to one or more examples of the present disclosure.

Referring to FIG. 20, in some examples, the apparatus 300 is configured to facilitate ease-of-assembly, compactness, and reliability of electrical components that are electrically coupled to the circuit board 100. The circuit board 100 has a unique shape to facilitate the functionality of the apparatus 300. For example, in the illustrated implementations, the circuit board 100 has a fork-like shape. More specifically, the circuit board 100 includes a pronged portion 313 and a neck portion 315 in certain examples. The neck portion 315 extends in a lengthwise direction L from the pronged portion 313 and the pronged portion 313 is wider, in a widthwise direction W, than the neck portion 315.

The pronged portion 313 includes opposing prongs 317 that are spaced apart from each other, parallel to each other, and extend in the lengthwise direction L away from the neck portion 315. The second electronic component 200b and the third electronic component 200c are end mounted to a respective one of the opposing prongs 317. The first electronic component 200a is end mounted to a middle portion 319 of the pronged portion 313 that is interposed between the opposing prongs 317 such that the first electronic component 200a is interposed between the opposing prongs 317. The middle portion 319 is shorter than the opposing prongs 317 in the lengthwise direction L such that the opposing prongs 317 extend beyond the middle portion 319 in the lengthwise direction L. As shown, there are gaps 321 defined between the middle portion 319 (and the first electronic component 200a) and the opposing prongs 317. Such a configuration enables the distal extent of the second electronic component 200b and the third electronic component 200c to be co-planar with the distal extent of the first electronic component 200a. In certain examples, however, the pronged portion 313 is configured to enable the distal extent of the second electronic component 200b and the third electronic component 200c to be non-coplanar with the distal extent of the first electronic component 200a (e.g., have a specific offset from coplanarity with the distal extent of the first electronic component 200a in a lengthwise direction L).

The circuit board 100 can include electrical traces 362 formed on the top major surface 110a that extend from the pronged portion 313 to the neck portion 315. In certain examples, at least a portion of the traces 362 are formed on a surface layer below and parallel to the top major surface 110a, enabling the top major surface 110a to function as a non-conductive electrical insulator to protect the traces 362. The circuit board 100 may also include electrical vias that electrically couple the pads 102 on the bottom major surface 110b to corresponding ones of the electrical traces 362, which are either on the top major surface 110a or on an underlying layer parallel to and below the top major surface 110a. In this manner, electrical connectivity of the first electrical component 200a is established through the electrical traces 362. The electrical traces 362 terminate at corresponding termination pads 364 formed on the top major surface 110a of the neck portion 315. The termination pads 364 are aligned and spaced apart in the widthwise direction W along the neck portion 315.

The apparatus 300 additionally includes a plurality of electrical wires 366. Each one of the wires 366 corresponds with one of the termination pads 364. In the illustrated implementation, the apparatus 300 includes four electrical traces 362, four termination pads 364, and four electrical wires 366. Each one of the wires 366 is electrically coupled to a corresponding one of the termination pads 364, such as via a soldered connection, to electrically connect the first electrical component 100a and the plurality of electrical wires 366. Positioning the termination pads 364 at the neck portion 315 locates the soldering of the electrical wires 366 away from the solder balls 202 of the first electrical component 100a such that thermal stress on the solder balls 202, caused by the soldering of the electrical wires 366 to the termination pads 364, is reduced. Additionally, positioning the termination pads 364 at the neck portion 315 enables the electrical wires 366 to be soldered to the termination pads 364 with the central axis of the electrical wires 366 parallel to the termination pads 364 and the major surfaces of the circuit board 100. Such a configuration promotes compactness and a streamlined design of the apparatus 300. Furthermore, because the length of the electrical traces 362 can be controlled to have a consistent length and spacing, improved impedance control of the circuit can be accomplished. The wires 366 can be jacketed or bonded together along at least a portion of the length of the wires 366. In some configuration, the wires 366 are replaced by an extended length circuit board 100 with extended electrical traces 362. The wires 366, when used, can be discrete wires or coaxial wires.

Additionally, referring to FIG. 20, in certain examples, the apparatus 300 includes a capacitor 360 that is mounted onto the top major surface 110a in electrical communication with the electrical traces 362. In certain examples, the capacitor 360 is a decoupling capacitor that helps mitigate interference and signal/image degradation associated with the first electrical component 200a. Mounting the capacitor 360 onto the top major surface 110a allows for a compact and streamlined design. Moreover, mounting the capacitor 360 in close proximity to (e.g., as close as practical to) the solder balls 202 of the first electrical component 200a and corresponding solder fillets 302 (and thus in close proximity to the first electrical component 200a) promotes the efficacy of the capacitor 360. In some examples, the capacitor 360 can be soldered to the circuit board 100 using the same solder fillets 302 used to solder the first electrical component 200a to the circuit board 100.

According to one example, a method of making the apparatus 300 includes positioning the second electrical component 200b and the third electrical component 200c on the corresponding minor surfaces 115 of the circuit board 100, applying solder paste between the second and third electrical components and the circuit board 100 (e.g., pads on the circuit board 100), and reflowing the solder paste via the application of heat. Then, the first electrical component 200a is positioned on the corresponding minor surface 115 of the circuit board 100, solder paste is applied between the first electrical component and the circuit board 100 (e.g., pads on the circuit board 100), and the solder paste is reflowed via the application of heat to form a sub-assembly. The sub-assembly is mounted in the tip housing 404 and an adhesive (e.g., glue, such as UV acrylic epoxy) is used to tack the sub-assembly in place in the tip housing 404. In certain implementations, such as where the first electrical component 200a is sensitive to UV glue or light, the adhesive is applied to the second and third electrical components 200b, 200c, but not to the first electrical component 200a, to prevent damage to an exterior coating of the first electrical component 200a or prevent the adhesive from penetrating the first electrical component 200a. In some examples, an opaque epoxy (e.g., black epoxy) is back-filled against the first electrical component 200a and within the tip housing 404 to further stabilize the sub-assembly in the tip housing 404.

Prior to soldering at least the first electrical component 200a to the printed circuit board, in some implementations, the method additionally includes mounting a support bracket (e.g., one of the support bracket 332 or the support bracket 350) to the circuit board 100. Additionally, the method can include, instead of or in addition to mounting the support bracket, forming one or more gussets 310 after soldering the first electrical component 200a to the printed circuit board.

Figure 21:
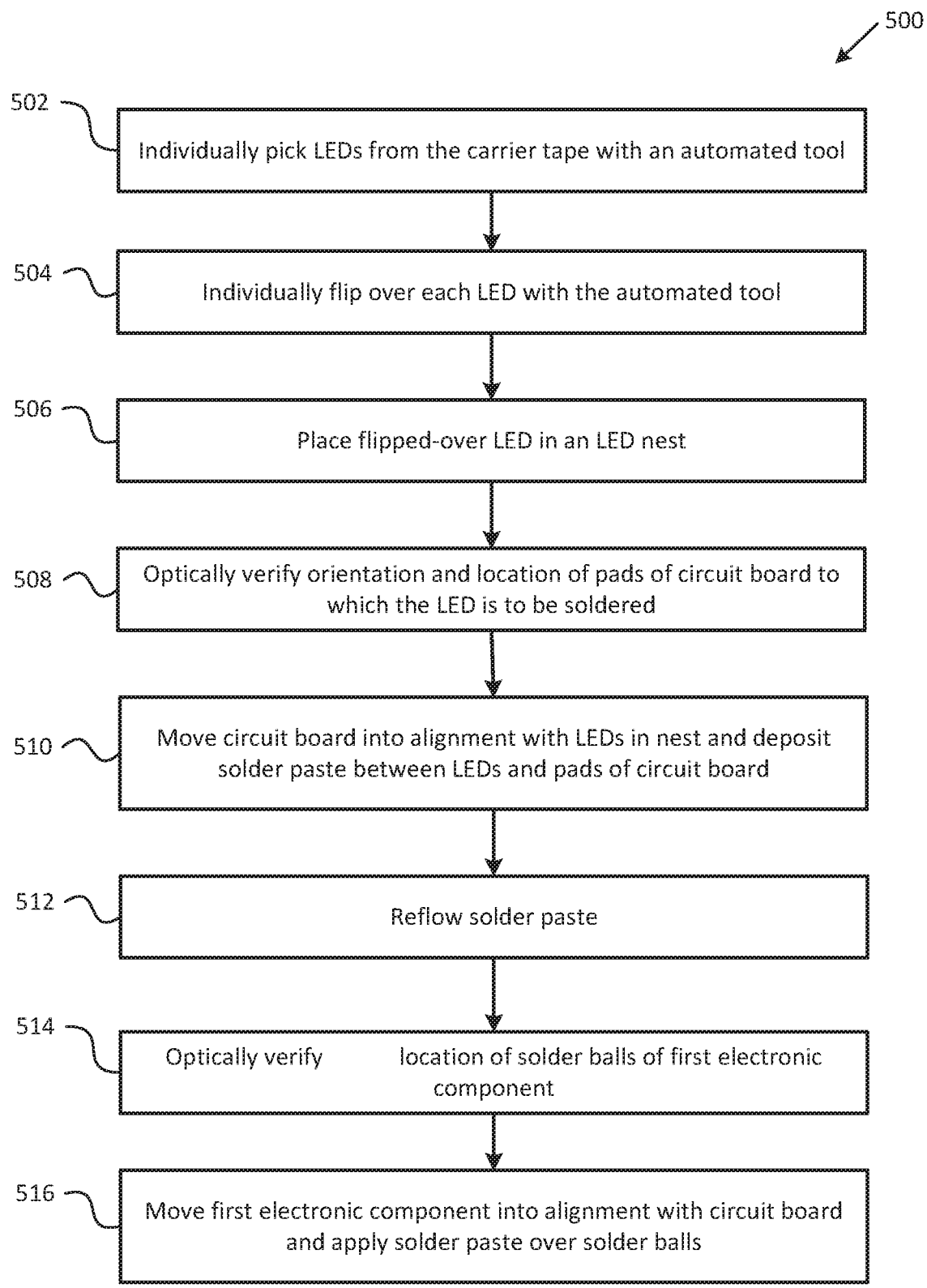
FIG. 21 illustrates a method of automatically making an apparatus, with electrical components end mounted to a printed circuit board, according to one or more examples of the present disclosure.

Although the method can be performed manually, in some implementations, the method is performed in an automated fashion using an automated tool (e.g., robotic arm). Referring to FIG. 21, according to one implementation of a method 500 of automatically making the apparatus 100, the second electronic component 200b and the third electronic component 200c are light-emitting diodes (LEDs). The LEDs are pre-arranged in industry standard carrier tape with a consistent physical orientation determined by the electrical polarity of the LEDs. The method 500 includes (block 502) individually picking each LED from the carrier tape with an automated tool, (block 504) individually flipping over (e.g., rotating 180-degrees) each LED with and relative to the automated tool, and (block 506) placing the flipped-over LED in an LED nest with the automated tool. The LED nest includes a plurality of the LEDs arranged in a predetermined pattern corresponding with a pattern of electrical contact pads on the printed circuit board 100.

The same, or another, automated tool picks up the circuit board 100 and, to reduce the effects of part manufacturing variation, a sensor optically verifies the orientation and location of the pads 102 to which the LED is to be soldered according to (block 508) of the method 500. According to (block 510) of the method 500, and based on the verified orientation and location of the pads 102, the automated tool then moves the circuit board 100 such that the pads 102 are aligned with the LEDs in the nest and the solder paste is deposited as described above. An automated laser then reflows the solder paste according to (block 512) of the method 500. This process is repeated for each one of the solder fillets 302 associated with the LEDs of a given apparatus 100. The automated method 500 then includes using a sensor to (block 514) optically verify the location of the solder balls 202 of the first electronic component 200a. According to (block 516) of the method 500, based on the verified orientation and the verified location of the electrical contact pads on the printed circuit board 100 and the verified location of the solder balls of the camera, the first electronic component 200a is then moved such that the solder balls are aligned alignment with corresponding pads of the circuit board 100 (it being in a verified orientation and location) for receiving solder paste to form the solder fillets 302.

Reference throughout this specification to features, advantages, or similar language does not imply that all of the features and advantages that may be realized with the subject matter of the present disclosure should be or are in any single embodiment. Rather, language referring to the features and advantages is understood to mean that a specific feature, advantage, or characteristic described in connection with an embodiment is included in at least one embodiment of the present disclosure. Thus, discussion of the features and advantages, and similar language, throughout this specification may, but do not necessarily, refer to the same embodiment.

In the above description, certain terms may be used such as "up," "down," "upper," "lower," "horizontal," "vertical,"

"left," "right," "over," "under" and the like. These terms are used, where applicable, to provide some clarity of description when dealing with relative relationships. But, these terms are not intended to imply absolute relationships, positions, and/or orientations. For example, with respect to an object, an "upper" surface can become a "lower" surface simply by turning the object over. Nevertheless, it is still the same object. Further, the terms "including," "comprising," "having," and variations thereof mean "including but not limited to" unless expressly specified otherwise. An enumerated listing of items does not imply that any or all of the items are mutually exclusive and/or mutually inclusive, unless expressly specified otherwise. The terms "a," "an," and "the" also refer to "one or more" unless expressly specified otherwise. Further, the term "plurality" can be defined as "at least two." Moreover, unless otherwise noted, as defined herein a plurality of particular features does not necessarily mean every particular feature of an entire set or class of the particular features.

Additionally, instances in this specification where one element is "coupled" to another element can include direct and indirect coupling. Direct coupling can be defined as one element coupled to and in some contact with another element. Indirect coupling can be defined as coupling between two elements not in direct contact with each other, but having one or more additional elements between the coupled elements. Further, as used herein, securing one element to another element can include direct securing and indirect securing. Additionally, as used herein, "adjacent" does not necessarily denote contact. For example, one element can be adjacent another element without being in contact with that element.

As used herein, the phrase "at least one of", when used with a list of items, means different combinations of one or more of the listed items may be used and only one of the items in the list may be needed. The item may be a particular object, thing, or category. In other words, "at least one of" means any combination of items or number of items may be used from the list, but not all of the items in the list may be required. For example, "at least one of item A, item B, and item C" may mean item A; item A and item B; item B; item A, item B, and item C; or item B and item C. In some cases, "at least one of item A, item B, and item C" may mean, for example, without limitation, two of item A, one of item B, and ten of item C; four of item B and seven of item C; or some other suitable combination.

Unless otherwise indicated, the terms "first," "second," etc. are used herein merely as labels, and are not intended to impose ordinal, positional, or hierarchical requirements on the items to which these terms refer. Moreover, reference to, e.g., a "second" item does not require or preclude the existence of, e.g., a "first" or lower-numbered item, and/or, e.g., a "third" or higher-numbered item.

As used herein, a system, apparatus, structure, article, element, component, or hardware "configured to" perform a specified function is indeed capable of performing the specified function without any alteration, rather than merely having potential to perform the specified function after further modification. In other words, the system, apparatus, structure, article, element, component, or hardware "configured to" perform a specified function is specifically selected, created, implemented, utilized, programmed, and/or designed for the purpose of performing the specified function. As used herein, "configured to" denotes existing characteristics of a system, apparatus, structure, article, element, component, or hardware which enable the system, apparatus, structure, article, element, component, or hardware to perform the specified function without further modification. For purposes of this disclosure, a system, apparatus, structure, article, element, component, or hardware described as being "configured to" perform a particular function may additionally or alternatively be described as being "adapted to" and/or as being "operative to" perform that function.

The present subject matter may be embodied in other specific forms without departing from its spirit or essential characteristics. The described embodiments are to be considered in all respects only as illustrative and not restrictive. All changes which come within the meaning and range of equivalency of the claims are to be embraced within their scope.

What is claimed is:

1. An apparatus comprising:
    a printed circuit board having a first major surface, a second major surface opposite the first major surface, and a minor surface perpendicular to the first major surface and the second major surface;
    an electronic component comprising a ball grid array, having spaced apart solder balls, on a mounting surface of the electronic component, wherein the electronic component is mounted to the minor surface of the printed circuit board such that the mounting surface is parallel to the minor surface and perpendicular to the first major surface and the second major surface, and the solder balls of the ball grid array are electrically connected to both the first major surface and the second major surface of the printed circuit board; and
    gussets, wherein a first one of the gussets is between and in contact with the electronic component and the first major surface and a second one of the gussets is between and in contact with the electronic component and the second major surface.

2. The apparatus of claim 1, wherein the printed circuit board is flexible.

3. The apparatus of claim 1, wherein the gussets are made of an epoxy material.

4. The apparatus of claim 1, wherein:
    the first one of the gussets is between and in contact with the mounting surface of the electronic component and the first major surface of the printed circuit board; and
    the second one of the gussets is between and in contact with the mounting surface of the electronic component and the second major surface of the printed circuit board.

5. The apparatus of claim 4, wherein the first one and the second one of the gussets are interposed between and do not overlay the solder balls of the ball grid array.

6. The apparatus of claim 4, wherein each one of the first one and the second one of the gussets is interposed between and overlays respective ones of the solder balls of the ball grid array.

7. The apparatus of claim 1, wherein:
    the electronic component comprises opposing side surfaces that are angled relative to the mounting surface;
    the first one of the gussets is between and in contact with a first one of the opposing side surfaces of the electronic component and the first major surface; and
    the second one of the gussets is between and in contact with a second one of the opposing side surfaces of the electronic component and the first major surface.

8. The apparatus of claim 7, wherein:
    a third one of the gussets is between and in contact with the first one of the opposing side surfaces of the electronic component and the second major surface; and a fourth one of the gussets is between and in contact with the second one of the opposing side surfaces of the electronic component and the second major surface.

9. The apparatus of claim 8, wherein:
a fifth one of the gussets is between and in contact with the mounting surface of the electronic component and the first major surface of the printed circuit board; and
a sixth one of the gussets is between and in contact with the mounting surface of the electronic component and the second major surface of the printed circuit board.

10. The apparatus of claim 1, further comprising a capacitor mounted onto the first major surface of the printed circuit board, in close proximity to the electronic component, and electrically coupled with the electronic component to mitigate interference and signal or image degradation associated with the electronic component.

11. An apparatus comprising:
a printed circuit board having a first major surface, a second major surface opposite the first major surface, and a minor surface perpendicular to the first major surface and the second major surface;
an electronic component comprising a ball grid array, having spaced apart solder balls, on a mounting surface of the electronic component, wherein the electronic component is mounted to the minor surface of the printed circuit board such that the mounting surface is parallel to the minor surface and perpendicular to the first major surface and the second major surface, and the solder balls of the ball grid array are electrically connected to both the first major surface and the second major surface of the printed circuit board; and
a support bracket in contact with the mounting surface of the electronic component, the first major surface of the printed circuit board, and the second major surface of the printed circuit board.

12. The apparatus of claim 11, wherein the support bracket is perpendicular to the printed circuit board.

13. The apparatus of claim 11, wherein the support bracket is interposed between the solder balls of the ball grid array.

14. The apparatus of claim 11, wherein:
the printed circuit board comprises a first slot formed in and extending from the minor surface of the printed circuit board;
the support bracket comprises a second slot;
the support bracket is received in the first slot of the printed circuit board; and
the printed circuit board is received in the second slot of the support bracket.

15. The apparatus of claim 11, wherein:
the support bracket comprises an intermediate portion and a supplemental engagement portion;
the intermediate portion is in contact with the mounting surface of the electronic component; and
the supplemental engagement portion wraps around at least a portion of the electronic component.

16. The apparatus of claim 15, wherein the intermediate portion is perpendicular to the supplemental engagement portion.

17. The apparatus of claim 11, further comprising gussets, wherein a first one of the gussets is between and in contact with the electronic component and the first major surface and a second one of the gussets is between and in contact with the electronic component and the second major surface.

18. An apparatus comprising:
a printed circuit board having a first major surface, a second major surface opposite the first major surface, and a minor surface perpendicular to the first major surface and the second major surface;
an electronic component comprising a ball grid array, having spaced apart solder balls, on a mounting surface of the electronic component, wherein the electronic component is mounted to the minor surface of the printed circuit board such that the mounting surface is parallel to the minor surface and perpendicular to the first major surface and the second major surface, and the solder balls of the ball grid array are electrically connected to both the first major surface and the second major surface of the printed circuit board; and
a second electronic component and a third electronic component mounted to a second minor surface and a third minor surface of the printed circuit board, respectively, wherein the second minor surface and the third minor surface are parallel to the minor surface of the printed circuit board.

19. The apparatus of claim 18, wherein:
the electronic component is interposed between the second electronic component and the third electronic component;
the second minor surface and the third minor surface of the printed circuit board are spaced apart from the minor surface of the printed circuit board;
the second minor surface and the third minor surface of the printed circuit board are defined by an end of a corresponding one of two prongs of the printed circuit board; and
the two prongs extend away from the minor surface of the printed circuit board in a direction perpendicular to the minor surface.

20. The apparatus of claim 18, wherein the electronic component is a camera, the second electronic component is a first light-emitting diode (LED), and the third electronic component is a second LED.

21. A method of automatically making an apparatus, the method comprising:
individually picking light-emitting diodes (LEDs) from a carrier tape, comprising a plurality of LEDs, with an automated tool;
individually flipping over each one of the LEDs picked from the carrier tape with and relative to the automated tool;
after flipping over each one of the LEDs, placing the LEDs relative to each other to form an LED nest comprising a plurality of LEDs arranged in a predetermined pattern corresponding with a pattern of electrical contact pads on a printed circuit board;
optically verifying an orientation and a location of electrical contact pads of a printed circuit board using a sensor;
based on a verified orientation and a verified location of the electrical contact pads, moving the printed circuit board, with the automated tool or a second automated tool, such that corresponding ones of the electrical contact pads of the printed circuit board are aligned with the LEDs in the LED nest;
applying solder paste to the corresponding ones of the electrical contact pads and the LEDs;
reflowing the solder paste applied to the electrical contact pads and the LEDs;
optically verifying a location of solder balls of a camera, using the sensor or a second sensor;
based on the verified orientation and the verified location of the electrical contact pads and a verified location of the solder balls of the camera, moving the camera such that the solder balls of the camera are aligned with corresponding ones of the electrical contact pads;

applying solder paste to the solder balls and the electrical contact pads aligned with the solder balls; and reflowing the solder paste applied to the solder balls and the electrical contact pads aligned with the solder balls.

\* \* \* \* \*